(12) United States Patent
Kitahara et al.

(10) Patent No.: US 12,378,275 B2
(45) Date of Patent: *Aug. 5, 2025

(54) POROUS INORGANIC CARRIER AND METHOD FOR PRODUCING NUCLEIC ACID USING SAME

(71) Applicant: SUMITOMO CHEMICAL COMPANY, LIMITED, Chuo-ku (JP)

(72) Inventors: Masaki Kitahara, Chuo-ku (JP); Takeshi Yoshioka, Osaka (JP); Takashi Hara, Osaka (JP); Takashi Arimura, Tsukuba (JP); Takeshi Ishiyama, Ichihara (JP); Hiroshi Kishida, Niihama (JP)

(73) Assignee: SUMITOMO CHEMICAL COMPANY, LIMITED, Chuo-ku (JP)

( * ) Notice: Subject to any disclaimer, the term of this patent is extended or adjusted under 35 U.S.C. 154(b) by 814 days.

This patent is subject to a terminal disclaimer.

(21) Appl. No.: 17/599,787

(22) PCT Filed: Feb. 28, 2020

(86) PCT No.: PCT/JP2020/008321
§ 371 (c)(1),
(2) Date: Sep. 29, 2021

(87) PCT Pub. No.: WO2020/202951
PCT Pub. Date: Oct. 8, 2020

(65) Prior Publication Data
US 2022/0106347 A1    Apr. 7, 2022

(30) Foreign Application Priority Data

Mar. 29, 2019   (JP) ................. 2019-067995

(51) Int. Cl.
| | | |
|---|---|---|
| C07H 21/00 | (2006.01) | |
| C01B 33/157 | (2006.01) | |
| C07F 7/18 | (2006.01) | |
| C07H 1/02 | (2006.01) | |
| C07H 21/04 | (2006.01) | |

(52) U.S. Cl.
CPC ................. *C07H 1/02* (2013.01); *C07F 7/18* (2013.01); *C07H 21/04* (2013.01)

(58) Field of Classification Search
None
See application file for complete search history.

(56) References Cited

U.S. PATENT DOCUMENTS

| | | |
|---|---|---|
| 6,995,259 B1 | 2/2006 | Vargeese et al. |
| 7,205,399 B1 | 4/2007 | Vargeese et al. |
| 7,777,023 B2 | 8/2010 | Vargeese et al. |
| 2004/0127357 A1 | 7/2004 | Simpson et al. |
| 2009/0005536 A1 | 1/2009 | Rothstein et al. |
| 2011/0092690 A1 | 4/2011 | Hayakawa et al. |
| 2014/0235435 A1 | 8/2014 | Miyahara et al. |

FOREIGN PATENT DOCUMENTS

| | | | |
|---|---|---|---|
| CA | 3052561 A1 * | 8/2018 | ............. A61K 31/00 |
| CN | 102060699 A | 5/2011 | |
| CN | 103906708 A | 7/2014 | |
| CN | 108176387 A | 6/2018 | |
| EP | 2 772 466 A1 | 9/2014 | |
| JP | 2958338 B | 10/1999 | |
| JP | 2006-502856 A | 1/2006 | |
| JP | 2011-88843 A | 5/2011 | |
| JP | WO 2013/062105 A1 | 5/2013 | |
| WO | WO 03/026775 A1 | 4/2003 | |
| WO | WO 2004/035170 A2 | 4/2004 | |
| WO | WO 2017/0119503 A1 | 7/2017 | |

(Continued)

OTHER PUBLICATIONS

Extended European Search Report issued Dec. 7, 2022 in European Patent Application No. 20783249.4, 9 pages.
Richard T. Pon, "Solid-Phase Supports for Oligonucleotide Synthesis," Methods in Molecular Biology, vol. 20, Protocols for Oligonucleotides and Analogs, Synthesis and Properties, XP009175601, 1993, 33 pages.
Combined Chinese Office Action and Search Report issued on Feb. 8, 2023 in Chinese Patent Application 202080024891.8 (with English translation), 20 pages.
International Search Report issued May 19, 2020 in PCT/JP2020/008321 (submitting English translation only), 2 pages.

(Continued)

*Primary Examiner* — Traviss C McIntosh, III
(74) *Attorney, Agent, or Firm* — Oblon, McClelland, Maier & Neustadt, L.L.P.

(57) ABSTRACT

An inorganic porous carrier including a linker of formula (1), wherein a mode diameter in a pore distribution is 0.04 μm to 1 μm, and a predetermined cumulative pore volume ratio is 30% or less [a bond * represents a linkage to the oxygen atom of a silanol group in an inorganic porous substance; n is an integer; R represents independently of each other an alkyl group containing 3 to 10 carbon atoms which may optionally have a substituent such as an alkoxy group; and L represents a single bond; an alkylene group of 1 to 20 carbon atoms; or an alkylene group containing 2 to 20 carbon atoms which contains —$CH_2$-Q-$CH_2$— group wherein any group Q selected from a group consisting of —O— etc. is inserted into at least one of —$CH_2$—$CH_2$— group constituting the alkylene group]; and a method for preparing a nucleic acid using the same.

(1)

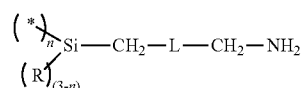

18 Claims, No Drawings
Specification includes a Sequence Listing.

(56) References Cited

FOREIGN PATENT DOCUMENTS

WO     WO-2017119503 A1 *   7/2017   ............. C12M 1/00

OTHER PUBLICATIONS

International Preliminary Report on Patentability and Written Opinion of the International Searching Authority issued Sep. 28, 2021 in PCT/JP2020/008321 (submitting English translation only), 7 pages.
International Search Report issued May 26, 2020 in PCT/JP2020/008313 (submitting English translation only), 3 pages.
International Preliminary Report on Patentability and Written Opinion of the International Searching Authority issued Sep. 28, 2021 in PCT/JP2020/008313 (submitting English translation only), 6 pages.
International Search Report issued May 19, 2020 in PCT/JP2020/008318 (submitting English translation only), 2 pages.
International Preliminary Report on Patentability and Written Opinion of the International Searching Authority issued Sep. 28, 2021 in PCT/JP2020/008318 (submitting English translation only), 7 pages.
International Search Report issued May 19, 2020 in PCT/JP2020/008323 (submitting English translation only), 2 pages.
International Preliminary Report on Patentability and Written Opinion of the International Searching Authority issued Sep. 28, 2021 in PCT/JP2020/008323 (submitting English translation only), 6 pages.
International Search Report issued May 19, 2020 in PCT/JP2020/008325 (submitting English translation only), 2 pages.
International Preliminary Report on Patentability and Written Opinion of the International Searching Authority issued Sep. 28, 2021 in PCT/JP2020/008325 (submitting English translation only), 6 pages.
J. Katzhendler, et al. "The Effect of Spacer, Linkage and Solid Support on the Synthesis of Oligonucleotides" Tetrahedron, vol. 45, No. 9, 1989, pp. 2777-2792.
Kiyohisa Imada, et al., "Studies on the Internal Surface of Porous Glass and Chemical Modification thereof" Journal of the Chemical Society of Japan, vol. 4, 1990, pp. 407-414 (with English translation).
Glenn Tong, et al., The Synthesis of Oligonucleotide-Polyamide Conjugate Molecules Suitable as PCR Primers, Journal of Organic Chemistry, vol. 58, No. 8, 1993, pp. 2223-2231.
J-Y. Wang, et al., "Preparation of a New Support for Solid Phase Synthesis of Glass Bead Surface with Amino" Hecheng Huaxue, Chinese Journal of Synthetic Chemistry, vol. 21, No. 1, 2013, pp. 66-69 (with English Abstract).
Roxana S. Timofte, et al., "Preparation of Silane-Grafted Pellets: Silica Bound Reagents in a Very Convenient Form" Tetrahedron Letters, vol. 45, 2004, pp. 39-42.
Chinese Office Action issued on Jul. 1, 2023 in Chinese Patent Application No. 202080024891.8 (with English translation), 16 pages.
Chinese Office Action issued on Oct. 19, 2023 in Chinese Patent Application No. 202080024891.8 (with English translation), 16 pages.
U.S. Appl. No. 17/599,409, filed Sep. 28, 2021, Takuya Miyagawa, et al.
U.S. Appl. No. 17/599,297, filed Sep. 28, 2021, Kanako Yamazaki, et al.
U.S. Appl. No. 17/599,700, filed Sep. 29, 2021, Takashi Arimura, et al.
U.S. Appl. No. 17/599,249, filed Sep. 28, 2021, Syusaku Hara, et al.

* cited by examiner

SEQUENCE LISTING

<160> NUMBER OF SEQ ID NOS: 3

<210> SEQ ID NO 1
<211> LENGTH: 23
<212> TYPE: RNA
<213> ORGANISM: Artificial Sequence
<220> FEATURE:
<223> OTHER INFORMATION: Synthesized RNA

<400> SEQUENCE: 1
gcagaguaca cacagcauau acc                                        23

<210> SEQ ID NO 2
<211> LENGTH: 25
<212> TYPE: RNA
<213> ORGANISM: Artificial Sequence -continued

```
<220> FEATURE:
<223> OTHER INFORMATION: Synthesized RNA

<400> SEQUENCE: 2
gguauaugcu guguguacuc ugcuu                                           25

<210> SEQ ID NO 3
<211> LENGTH: 103
<212> TYPE: RNA
<213> ORGANISM: Artificial Sequence
<220> FEATURE:
<223> OTHER INFORMATION: Syntesized RNA

<400> SEQUENCE: 3
auaacucaau uuguaaaaaa guuuuagagc uagaaauagc aaguuaaaau aaggcuaguc     60
cguuaucaac uugaaaaagu ggcaccgagu cggugcuuuu uuu                      103
```

POROUS INORGANIC CARRIER AND METHOD FOR PRODUCING NUCLEIC ACID USING SAME

CROSS-REFERENCE TO RELATED APPLICATIONS

The present application is a 35 U.S.C. § 371 national stage patent application of International patent application PCT/JP2020/008321, filed on Feb. 28, 2020, which is based on and claims the benefits of priority to Japanese Application No. 2019-067995, filed on Mar. 29, 2019. The entire contents of these applications are incorporated herein by reference.

TECHNICAL FIELD

This application claims priority to and the benefit of Japanese Patent Application No. 2019-067995 filed on Mar. 29, 2019, the entire contents of which are incorporated herein by reference.

The present invention relates to an inorganic porous carrier, and a method for preparing nucleic acid using the same.

BACKGROUND ART

As a method for chemically synthesizing a nucleic acid, a solid-phase synthesis method according to a phosphoramidite method is widely used. In this method, first, a functional group such as an amino group is introduced onto an inorganic porous substance by a silane coupling agent or the like, and a nucleoside providing a 3' end of the nucleic acid is bound to the functional group. Then, a nucleic acid elongation reaction is carried out on the solid-phase support by starting from the nucleoside.

In the solid-phase synthesis method, when a strand length of the nucleic acid to be synthesized becomes long, a synthesis efficiency drastically decreases, and consequently, a large amount of by-products (that is, a substance having shorter strand length than a target strand length) is prone to be produced and mixed. It is considered that this phenomenon is caused by closing a pore when a nucleic acid molecule is elongated in a pore of a porous carrier, resulting in an inhibition of elongation reaction, side reactions, or the like.

As a technique for preventing a closure of a pore due to an elongation of a nucleic acid molecule, it has been proposed that a swelling polymer is covered on the surface of an inorganic porous substance (see Patent document 1).

CITATION LIST

Patent Document

Patent Document 1: US 2009/0005536 A1

SUMMARY OF THE INVENTION

Problems to be Solved by Invention

In general, as a nucleic acid to be synthetized is longer, a closure of a pore has a tendency to be happened, and as a result, a purity on nucleic acid synthesis has a tendency to be decreased. In particular, when a long-strand nucleic acid having 40 mer or more is synthesized, in a case of using conventional solid-phase carrier, a nucleic acid having short strand length than a nucleic acid having a target strand length has a tendency to be produced, and as a result, a purity of the long length nucleic acid becomes a problem.

The present invention has been made in view of the above situation, and the problem to be solved by the present invention is to provide an inorganic porous carrier which can improve the purity in the preparation of nucleic acid, and a method for preparing a nucleic acid using the same.

Means to Solve Problems

In order to solve the above problem, the present invention have the following constituent aspects.

That is, in the first aspect of the present invention, the invention provides an inorganic porous carrier that comprises a linker represented by general formula (1), wherein a most frequent value (mode diameter) in a pore distribution as measured by mercury intrusion method is 0.04 μm to 1 μm, and also a cumulative pore volume ratio of cumulative pore volume (VB) whose pore size being within a range of 0.004 μm to 0.04 μm relative to cumulative pore volume (VA) whose pore size being within a range of 0.04 μm to 1 μm is 30% or less.

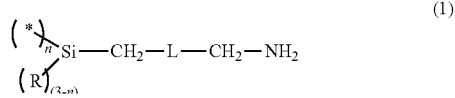

(1)

[wherein, a bond marked with * represents a linkage to the oxygen atom of a silanol group in an inorganic porous substance;

n is an integer of 1, 2 or 3;

R represents independently of each other an alkyl group containing 3 to 10 carbon atoms which may optionally have a substituent selected from an alkoxy group and a fluorine atom; a phenyl group which may optionally have a substituent selected from an alkyl group, an alkoxy group, and a fluorine atom; a hydroxyl group; or an alkoxy group containing 1 to 4 carbon atom; and L represents a single bond; an alkylene group of 1 to 20 carbon atoms; or an alkylene group containing 2 to 20 carbon atoms which contains —CH$_2$-Q-CH$_2$— group wherein any group Q selected from a group consisting of —O—, —NH—, —NH—CO— and —NH—CO—NH— is inserted into at least one of —CH$_2$—CH$_2$— group constituting the alkylene group; providing that a carbon atom of the methylene group bound to the group Q does not bind to another group Q at the same time].

In the second aspect of the present invention, the invention provides an inorganic porous carrier that comprises a linker represented by general formula (2), wherein a mode diameter in a pore distribution as measured by mercury intrusion method is 0.04 μm to 1 μm, and also a cumulative pore volume ratio of cumulative pore volume (VS) whose pore size being within a range of 0.004 μm to 0.04 μm relative to cumulative pore volume (VA) whose pore size being within a range of 0.04 μm to 1 μm is 30% or less (hereinafter, the inorganic porous carrier may be referred to as "Solid-phase carrier").

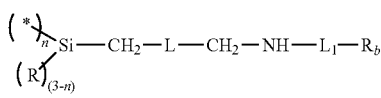

(2)

[wherein
a bond marked with * represents a linkage to the oxygen atom of a silanol group in an inorganic porous substance;
n is an integer of 1, 2 or 3;
R represents independently of each other an alkyl group containing 3 to 10 carbon atoms which may optionally have a substituent selected from an alkoxy group and a fluorine atom; a phenyl group which may optionally have a substituent selected from an alkyl group, an alkoxy group, and a fluorine atom; a hydroxyl group; or an alkoxy group containing 1 to 4 carbon atom;
L represents a single bond; an alkylene group containing 1 to 20 carbon atoms; or an alkylene group containing 2 to 20 carbon atoms which contains —$CH_2$-Q-$CH_2$— group wherein any group Q selected from the group consisting of —O—, —NH—, —NH—CO—, and —NH—CO—NH— is inserted into at least one —$CH_2$—$CH_2$— group constituting the alkylene group; providing that a carbon atom of the methylene group bound to the group Q doses not bind to another group Q at the same time;
$R_b$ represents a nucleotide or a nucleotide in which a reactive group is protected or deprotected; and
$L_1$ represents a divalent group bound to an oxygen atom of a primary or a secondary hydroxy group as $R_b$.].

According to a certain one embodiment of the second aspect of the present invention, $L^1$ in the general formula (2) may be a succinyl linker or a universal linker.

According to a certain one embodiment of the second aspect of the present invention, the specific surface area per volume of the above-mentioned inorganic porous substance may be within a range of 0.1 $m^2$/mL or more to 100 $m^2$/mL or less.

According to a certain one embodiment of the second aspect of the present invention, the pore volume per volume of the above-mentioned inorganic porous substance may be within a range of 0.05 mL/mL or more to 0.6 mL/mL or less.

According to a certain one embodiment of the second aspect of the present invention, the porosity of the above-mentioned inorganic porous substance may be 50% or more.

According to a certain one embodiment of the second aspect of the present invention, a density of the above-mentioned grafted linker may be within a range of 0.1 μmol/$m^2$ or more to 5.0 μmol/$m^2$ or less relative to a specific surface area per mass of the inorganic porous substance.

According to a certain one embodiment of the second aspect of the present invention, a particle diameter (a median diameter) of the inorganic porous substance may be within a range of 1 μm or more to 1000 μm or less. According to a certain one embodiment of the second aspect of the present invention, the inorganic porous substance may be silica, silica gel, zeolite, or glass.

In the third aspect of the present invention, a method for preparing a nucleic acid is provided, which is carried out using the inorganic porous carrier wherein $R_b$ in the general formula (2) represents a nucleoside or nucleotide in which a hydroxyl group as a reactive group is protected, wherein the method comprises the following steps:

a step (A) of deprotecting a protecting group of the hydroxyl group at a 5' position of the nucleoside;
a step (B) of subjecting the hydroxyl group at the 5' position of the nucleoside produced in the step (A) to a condensation reaction with an amidite compound having a second nucleoside base to produce a phosphite;
a step (C) of oxidizing the phosphite produced in the step (B) to produce a nucleotide; and
a step (D) of deprotecting a protecting group of a hydroxyl group at a 5' position of the nucleotide produced in the step (C).

In one embodiment according to the third aspect of the present invention, the method for preparing nucleic acid may further comprise the following steps:

a step (B') of subjecting the product produced in the step (D) to a condensation reaction with an amidite compound having a nucleoside base to be introduced in next time to produce a phosphite;
a step (C') of oxidizing the phosphite produced in the step (B') to produce an oligonucleotide; and
a step (D') of deprotecting a protecting group of a hydroxyl group at a 5' position in an end of an oligonucleotide strand produced in the step (C').

In one embodiment according to the third aspect of the present invention, the method for preparing nucleic acid may further comprise a step (E) of carrying out a series of steps consisting of the above step (B'), step (C') and step (D') repeatedly m times (wherein m is an integer of 1 or more) to react the number of m of amidite compounds, and then cleaving an elongated nucleic acid.

In the fourth aspect of the present invention, it is provided a use of the inorganic porous carrier according to the first aspect or a solid-phase carrier according to the second aspect in a preparation of a nucleic acid by a phosphoramidite method.

Effect of Invention

The inorganic porous carrier according to the present invention can further improve the purity of nucleic acid in the preparation of nucleic acid.

The method for preparing nucleic acid according to the present invention can further improve the purity of nucleic acid, and particularly obtain a long-strand nucleic acid in high yield.

MODE FOR CARRYING OUT THE INVENTION

As used herein, when a certain numerical range is referred to as "A to B" or "A-B", it means a range represented by "from A or more to B or less" unless otherwise stated.
(Inorganic Porous Carrier)

The inorganic porous carrier of the first aspect of the present invention is explained.
<Inorganic Porous Substance>

The inorganic porous substance constituting the inorganic porous carrier of the present embodiment is an inorganic porous substance wherein a mode diameter in a pore distribution as measured by mercury intrusion method is 0.04 μm to 1 μm, and also a cumulative pore volume ratio of cumulative pore volume (VB) whose pore size being within a range of 0.004 μm to 0.04 μm relative to cumulative pore volume (VA) whose pore size being within a range of 0.04 μm to 1 μm is 30% or less.

The inorganic porous substance has typically a silanol group that can support a silane coupling agent. As a typical examples of the inorganic porous substance, silica, silica gel, zeolite, glass, or quartz is exemplified, preferably silica, silica gel, zeolite or glass is exemplified. These compounds may be used as a commercially available product, or may be used as one obtained by preparing according to the below-mentioned synthesis method.

[Method for Preparing Inorganic Porous Substance Containing Silanol Group]

Examples of the method for preparing the inorganic porous substance containing the silanol group include a dry method and a wet method. Specific examples of the former include a combustion method and an arc method, and specific examples of the latter include synthesis methods such as a precipitation method, a sol-gel method, and a hydrothermal synthesis method (Reference: TOSOH Research & Technology Review Vol. 45 (2001).).

The preparation of such an inorganic porous substance is carried out by, for example, using silicate, alkoxysilane, chlorosilanes or the like as raw materials according to the synthesis method as described above using a solvent and a template.

The preparation of the inorganic porous substance can be carried out, for example, according to any one of the following methods: 1. a method of precipitating silica, and then removing a solvent contained in a framework of the silica; 2. a method of precipitating a solid after mixing silica with dissimilar metal other than silica such as aluminum, boron, or the like, and then phase-separating the resulting mixture into a silica component and a component other than silica, and removing the component other than silica; 3. a method of precipitating silica after mixing silica with an ammonium salt or a polymer as a template agent, and then removing the template agent; and 4. a method of aggregating a precipitated silica. A combination of two or more of the above methods may be used.

The methods of removing the solvent or the template agent in the above methods 1 and 3 may include drying, supercritical extraction, calcining or the like.

As silica which is aggregated by the method 4, silica, silica gel, zeolite, glass or quartz, or two or more thereof may be used.

The zeolite is a substance containing silicon and oxygen as an element composed of the framework of the zeolite, and may be crystalline silica whose framework is substantially composed of silicon and oxygen, and may be crystalline metallosilicates and so on further containing other elements as a constitute element for the framework.

In the case of metallosilicate and so on, examples of the elements that may be existed as the element other than silicon and oxygen include anyone kind of the followings selected from Be, B, Al, Ti, V, Cr, Fe, Co, Ni, Cu, Zn, Ga, Ge, Zr, Nb, Sb, La, Hf or Bi, and as needed, two or more kinds of these elements may be contained.

Also, the atomic ratio of silicon against existing elements other than silicon and oxygen is preferably 5 or more, and further preferably 500 or more.

The above-mentioned zeolites may be synthesized by a hydrothermal synthesis of a mixture containing silicon compound, water and quaternary ammonium hydroxide.

Examples of the above-mentioned silicon compound include amorphous silica; alkaline silicates such as sodium silicate and potassium silicate; tetraalkyl orthosilicate such as tetramethyl orthosilicate, tetraethyl orthosilicate, tetrapropyl orthosilicate, and tetrabutyl orthosilicate, and as needed, two or more kinds of these compounds can be used.

Examples of the above-mentioned quaternary ammonium hydroxide preferably include tetraalkyl ammonium hydroxides. Examples of the tetraalkyl ammonium hydroxide include for example, tetramethyl ammonium hydroxide, tetraethyl ammonium hydroxide, n-propyl trimethyl ammonium hydroxide, tetra-n-propyl ammonium hydroxide, tetra-n-butyl ammonium hydroxide, triethyl methyl ammonium hydroxide, tri-n-propyl methyl ammonium hydroxide, and tri-n-butyl methyl ammonium hydroxide, or two or more kinds of these compounds.

The molar ratio of water relative to silicon in the mixture of the hydration synthesis is within a range of 5 to 100, more preferably 10 to 60.

The molar ratio of the quaternary ammonium ion relative to silicon in the mixture is preferably 0.1 to 0.6, and more preferably 0.2 to 0.5.

The molar ratio of the hydroxide ion relative to silicon in the mixture to be subjected to a hydration synthesis is adjusted to usually 0.1 to 0.6, preferably 0.2 to 0.5. As the molar ratio of the hydroxide ion relative to the silicon in the mixture is higher, the primary particle diameter of the obtained zeolite has a tendency to become small.

The molar ratio of potassium relative to the silicon in the mixture is adjusted to preferably 0 to 0.1, more preferably 0.04 to 0.1. The molar ratio of potassium relative to the silicon in the mixture can be adjusted appropriately, for example, by adjusting a used amount of the silicon compound, or adjusting the content of each rough material, particularly, potassium compound which may be contained as impure material in the quaternary ammonium hydroxide.

When the mixture is subjected to a hydration synthesis reaction, the temperature of the hydration synthesis is preferably 80 to 160° C., more preferably 100 to 140° C. The duration of the hydration synthesis is preferably 1 to 200 hours, more preferably 12 to 72 hours. The pressure of the hydration synthesis is preferably within a range of 0.10 to 1.0 MPa as an absolute pressure, more preferably 0.11 to 0.50 MPa.

The method for hydration synthesis is not particularly limited, and, for example, can be carried out by enclosing the above-mentioned mixture into a reactor such as autoclave and then subjecting the resulting mixture to the reaction in a sealed state under the above-mentioned temperature condition while stirring.

The inorganic porous substance which is obtained by any one of the method of 1. to 4. in the above-mentioned preparation for inorganic porous substance or two or more thereof in combination is preferably in a form of particles, and may be formed into a spherical shape, or may be formed into a massive shape or a crushed shape, whereas, when they are used as carriers, the spherical shape or the crushed shape is preferable from the viewpoint of filling into a column for nucleic acid synthesis. The molding method is not particularly limited, but a spray drying method or an emulsion method may be used.

In this embodiment, a cumulative pore volume ratio (%) represents a value calculated by the following equation.

$$\text{Cumulative Pore Volume Ratio}(\%) = VB/VA \times 100$$

[Mercury Intrusion Method]

A pore diameter of an inorganic porous substance can be determined as follows.

First, a container containing a sample is evacuated in vacuum and the container is filled with mercury. A mercury has a high surface tension, and a mercury does not infiltrate into a pore of surface of the sample in situ (normal pressure), however, as a pressure applies to mercury and a pressure is increased gradually, a mercury is infiltrating gradually into a pore from a pore having a large diameter to a pore having a small pore. By measuring a press-fitting amount f mercury into a pore while a pressure is being increased continuously, a curve of mercury press-fitting curve is obtained from a correlation between a pressure applied to mercury and a press-fitting amount of mercury.

Here assuming that a shape of a pore is a cylindrical, when a pressure applied to a mercury is expressed as P, its pore size (pore diameter) is expressed as D, a surface tension of mercury is expressed as σ, a contact angle between a mercury and a sample is expressed as θ, a pore size (pore diameter) is expressed as the following equation (A).

$$D = -4\sigma \times \cos\theta / P \qquad (A)$$

In general, a surface tension of mercury: σ uses a value of 0.48 to 0.49 N/m, and a contact angle θ uses 13- to 140°.

Since σ and θ are both a constant value, a correlation between a pressure applied to mercury: P and a pore diameter: D can be determined by an equation A. By measuring an infiltrate volume of mercury at that moment, a pore volume can be calculated. That is, since there is correlation between the pressure applied to mercury: P and the pore diameter infiltrated by mercury: D, a pore distribution curve, which indicates a correlation between a size and a volume with respect to a pore diameter of the sample, can be obtained based on a curve of mercury press-fitting curve.

Here an approximate measurement limit of the pore diameter by a memory intrusion method is set to be about 0.004 μm or less as a lower limit and about 200 μm as an upper limit. A measurement by a mercury intrusion method can be carried out with a device such as a mercury porosimeter. Specific examples of the mercury porosimeter include AutoPoreIV9520 (manufactured by Micromeritics).

The inorganic porous substance according to this embodiment has a most frequent value (a mode diameter) of a pore size of 0.04 μm to 1 μm, preferably 0.04 μm to 0.5 μm, more preferably 0.04 μm to 0.3 μm in a pore distribution determined by a mercury intrusion method.

When the mode diameter is the lower limit value or more which is included within the above range, a steric hindrance between oligonucleic acids in a pore is unlikely to occur during the nucleic acid elongation reaction, the elongation reaction can easily proceed stably to achieve the target chain length. Whilst, when the mode diameter is the upper limit value or less which is included within the above range, it is easy to keep the surface area as a carrier which is sufficient for obtaining oligonucleic acid.

The mode diameter represents a pore size determined from a value of X-axis at a peak top in the pore size distribution obtained by the mercury intrusion method (a graph in which the X-axis is a value of the pore size and the Y-axis is a value obtained by differentiating the pore volume by the pore size).

Also, in the inorganic porous substance according to this embodiment, a cumulative pore volume ratio of cumulative pore volume (VB) whose pore size being within a range of 0.004 μm to 0.04 μm relative to cumulative pore volume (VA) whose pore size being within a range of 0.04 μm to 1 μm is 30% or less, preferably 26% or less, and more preferably % or less. The lower the lower limit value of the cumulative pore volume ratio is, it becomes more preferable, and it is substantially 3% or more, for example.

When the cumulative pore volume ratio is the upper limit value or less which is included within the above range, that is, 30% or less, the homogeneity of the pore size is increased, and as a result, it becomes easier to obtain a nucleic acid having a target strand length, and can achieve a high purity.

A size of the inorganic porous substance is not particularly limited, but from the viewpoint of column filling efficiency in the solid-phase synthesis of nucleic acid, and liquid feeding rate in a column filling, and the like, a particle size (median diameter, the same shall apply hereinafter) which is measured by a laser diffraction method (scattering method) is preferably within a range of 1 to 1000 μm, more preferably 5 to 500 μm, and further more preferably 10 to 300 μm.

The pore volume of the inorganic porous substance of the present embodiment is not particularly limited. Generally, in order to improve the productivity of nucleic acid per column, it is preferable that the pore volume per volume of the inorganic porous substance (mL/mL) is high regardless of the strand length of the nucleic acid. The pore volume per volume of the inorganic porous substance is preferably within a range of 0.05 to 0.6 mL/mL, and more preferably 0.05 to 0.5 mL/mL.

The pore volume per volume of the inorganic porous substance is determined by multiplying the bulk density (g/mL), which is measured by the mercury intrusion method, by the cumulative pore volume (VA) (mL/g) of pore having a pore size within a range of 0.04 μm to 1 μm.

A porous substance having a pore size of 0.04 μm or more is used as the inorganic porous substance. The inorganic porous substance to be used can be appropriately selected depending on the strand length of the nucleic acid to be synthesized. In general, when a strand length of the nucleic acid to be synthesized becomes long, it is preferable to select the inorganic porous substance having a large pore size. For example, when RNA of 40-mer to 200-mer is synthesized, the pore size is preferably within a range of 0.04 μm or more and 0.5 μm or less, and more preferably within a range of 0.04 μm or more and 0.3 μm or less.

The pore size (mode diameter) is determined based on a value of X-axis at a peak top in the pore size distribution obtained by the mercury intrusion method (a graph in which the X-axis is a value of the pore size and the Y-axis is a value obtained by calculating differentially the pore volume by the pore size).

The porosity of the inorganic porous substance is not particularly limited, and generally, in order to improve the productivity of nucleic acid per column, it is preferable that the porosity is high regardless of the strand length of the nucleic acid. The porosity is determined by the mercury intrusion method, and it is preferably 50% or more, and more preferably 70% or more.

The porosity herein is calculated based on the pore volume of pore having a pore size within a range of 0.004 to 200 μm, which is a range measured by the mercury intrusion method. That is, it is determined by multiplying the cumulative pore volume (mL/g) of pore having a pore size within the range of 0.004 μm to 200 μm by the bulk density (g/mL).

The inorganic porous carrier of the present embodiment contains a linker represented by the following general formula (1):

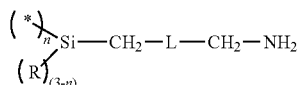
(1)

[wherein,
a bond marked with * represents a linkage to the oxygen atom of a silanol group in an inorganic porous substance;
n is an integer of 1, 2 or 3;
R represents independently of each other an alkyl group containing 3 to 10 carbon atoms which may optionally have a substituent selected from an alkoxy group and a fluorine atom; a phenyl group which may optionally have a substituent selected from an alkyl group, an alkoxy group, and a fluorine atom; a hydroxyl group; or an alkoxy group containing 1 to 4 carbon atom; and
L represents a single bond; an alkylene group of 1 to 20 carbon atoms; or an alkylene group containing 2 to 20 carbon atoms which contains —$CH_2$-Q-$CH_2$— group wherein any group Q selected from a group consisting of —O—, —NH—, —NH—CO— and —NH—CO—NH— is inserted into at least one of —$CH_2$—$CH_2$— group constituting the alkylene group; providing that a carbon atom of the methylene group bound to the group Q does not bind to another group Q at the same time].

In the formula (1), the alkyl group in each of R may be any of a linear alkyl group, a branched alkyl group or a cyclic alkyl group, and preferably a branched alkyl group so as to improve the yield easily. The alkyl group in each of $R^1$ and $R^2$ contains 3 to 10 carbon atoms, preferably 3 to 6 carbon atoms, and more preferably 3 or 4 carbon atoms.

Examples of the alkyl group in each of R include a linear alkyl group such as n-propyl group, n-butyl group, n-hexyl group and n-octyl group; a branched alkyl group such as isopropyl group, isobutyl group, sec-butyl group, tert-butyl group, 2-ethylhexyl group and 3,7-dimethyloctyl group; and a cyclic alkyl group such as cyclopropyl group and cyclohexyl group.

The substituent which may be optionally substituted on the alkyl group represented by each of R is an alkoxy group or a fluorine atom. Examples of the alkoxy group include an alkoxy group containing 1 to 3 carbon atoms.

The substituent which may be optionally substituted on the phenyl group represented by each of R is an alkyl group, an alkoxy group, or a fluorine atom. Examples of the alkyl group include an alkyl group containing 1 to 5 carbon atoms. Examples of the alkoxy group include an alkoxy group containing 1 to 3 carbon atoms.

In the case where n is 1 in the formula (1), a plural of R may be identical to or different from each other, and preferably identical to each other from the viewpoint of synthesis (for example, convenience and efficiency).

In the above-mentioned formula (1), an alkoxy group as R represents an alkoxy group containing 1 to 4 carbon atoms, preferably an alkoxy group containing 1 to 3 carbon atoms, and more preferably a methoxy group or an ethoxy group.

In the formula (1), the alkylene group in L may be any of a linear alkylene group or a branched alkylene group, and preferably a linear alkylene group so as to improve the yield easily. The alkylene group in L contains 1 to 20 carbon atoms, preferably 1 to 10 carbon atoms, and more preferably 1 to 6 carbon atoms.

Also an alkylene group as L may represent an alkylene group containing 2 to 20 carbon atoms which contains —$CH_2$-Q-$CH_2$— group wherein any group Q selected from a group consisting of —O—, —NH—, —NH—CO— and —NH—CO—NH— is inserted into at least one of —$CH_2$—$CH_2$— group constituting the alkylene group.

With the proviso that in this embodiment, in the linker represented by the above-mentioned general formula (1), a carbon atom of the methylene group bound to the group Q does not bond to another group Q at the same time.

As examples of the inorganic porous carrier, for example, any one of the following linkers represented by formulae (1-1), (1-2) or (1-3) or a plural forms selected from these linkers are exemplified.

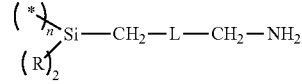
(1-1)

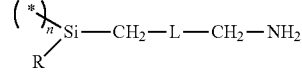
(1-2)

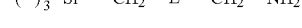
(1-3)

In the above-mentioned formula (1-1), (1-2) and (1-3), *, R and L have the same meanings as those of *, R and L as described in the above-mentioned formula (3).

The inorganic porous carrier of the present embodiment can be prepared, for example, by a method of treating a surface of the inorganic porous substance with a silane coupling agent represented by the following general formula (3).

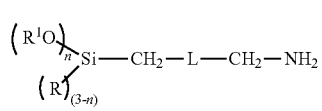
(3)

[wherein,
n is an integer of 1, 2 or 3;
R represents independently of each other an alkyl group containing 3 to 10 carbon atoms which may optionally have a substituent selected from an alkoxy group and a fluorine atom; a phenyl group which may optionally have a substituent selected from an alkyl group, an alkoxy group, and a fluorine atom; a hydroxyl group; or an alkoxy group containing 1 to 4 carbon atom;
$R^1$ represents independently of each other a hydrogen atom or al alkyl group;
L represents a single bond; an alkylene group of 1 to 20 carbon atoms; or an alkylene group containing 2 to 20 carbon atoms which contains —$CH_2$-Q-$CH_2$— group wherein any group Q selected from a group consisting of —O—, —NH—, —NH—CO— and —NH—CO—NH— is inserted into at least one of —$CH_2$—$CH_2$— group constituting the alkylene group; providing that a carbon atom of the methylene group bound to the group Q does not bind to another group Q at the same time].

In the above-mentioned formula (3), R and L have the same meanings as those of R and L as described in the above-mentioned formula (1).

The preparation of the inorganic porous carrier containing the linker represented by the general formula (1) is carried out, for example, by a method of mixing the inorganic porous substance with a certain silane coupling agent and a solvent, and then removing the solvent. In this case, the certain silane coupling agent is covalently bound to a silanol group on the surface of the inorganic porous substance by the mixing to form an inorganic porous carrier supporting the linker represented by the general formula (1).

Examples of the solvent as described above include acetonitrile, toluene, anisole, 2-heptanone, propyleneglycol monomethyl ether acetate, N,N-dimethylformamide, tetrahydrofuran, pentane, hexane, heptane, xylene, mesitylene, dichloromethane, chlorobenzene, water and the like, or a mixture of two or more thereof, and preferably include toluene.

within a range of 0.1 to 5.0 µmol/m², and preferably 0.5 to 2.0 µmol/m², relative to the specific surface area per mass of the inorganic porous substance, which is determined by $N_2$ adsorption/desorption measurement.

The silanol group which is not used in the reaction with the silane coupling agent, if needed, may be capped with a functional group which is inert to the nucleic acid synthesis, for example, trimethylsilyl group.

As described above, the surface of the inorganic porous substance can be treated with a certain silane coupling agent to produce the inorganic porous carrier which is modified with an aminosilyl group.

The silane coupling agent represented by the above general formula (3) can be prepared through the reaction route as shown below (synthetic route 1, synthetic route 2, or synthetic route 3).

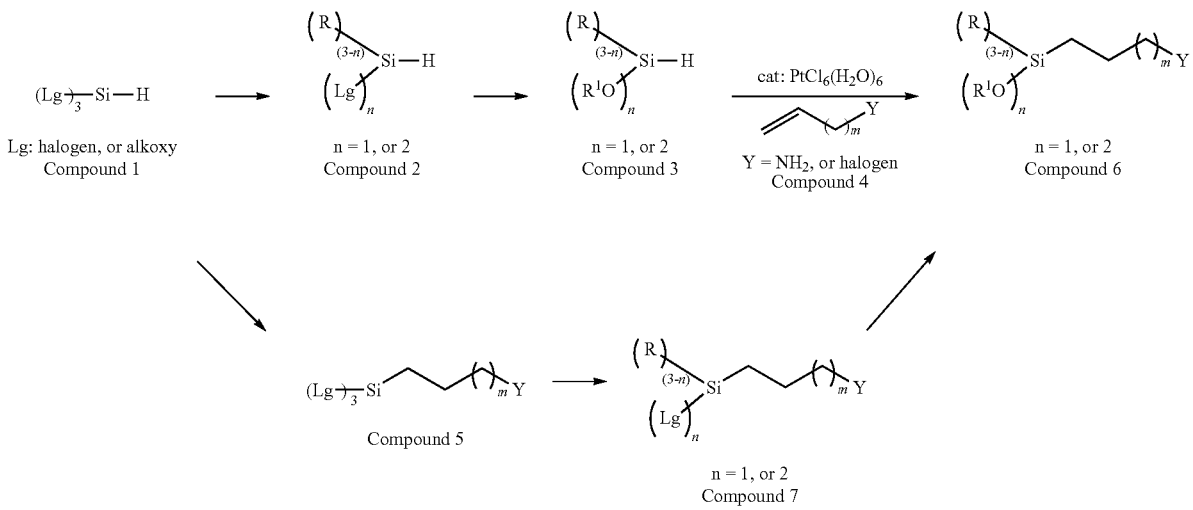

The above-mentioned inorganic porous substance and solvent are preferably used after being dehydrated from the viewpoint of suppressing a polymerization of the silane coupling agent as itself and facilitating the reaction of the silane coupling agent with the surface of the inorganic porous substance. The dehydration method is not particularly limited, but examples thereof include a method of heating the inorganic porous substance under reduced pressure; and a method of dispersing the inorganic porous substance in the solvent and then distilling off the solvent under normal pressure or reduced pressure to conduct an azeotrope dehydration.

When the inorganic porous substance is mixed with the silane coupling agent and the solvent, the mixture is usually heated to near the boiling point of the solvent to facilitate the reaction, but the temperature is not limited thereto, and the mixture may be mixed at room temperature, or in a state where it is cooled to room temperature or less.

The reaction of the inorganic porous substance with the silane coupling agent is usually carried out for about 1 to 12 hours, but in the case that the silane coupling agent containing an amino group is used, since the silane coupling agent as itself has a catalytic effect of facilitating the reaction, the reaction may be carried out for about a several minutes.

The amount of the silane coupling agent to be added is usually an amount in which a density of the grafted linker is Details of synthetic route 1 (Compound 1→Compound 2→Compound 3→Compound 6):

For example, when compound 1 is trichlorosilane, the compound 1 is reacted with an organolithium compound or an organomagnesium compound corresponding to R (nucleophilic substitution reaction) to obtain compound 2 (Step 1). Then, the compound 2 is reacted with $R^1OH$ (for example, methanol, ethanol, propanol, etc.) in the presence of a base, or is reacted with an alcoholate such as $R^1ONa$ or water ($R^1$: hydrogen) to obtain silane compound 3 (Step 2). Then, the compound 3 is subjected to a hydrosilylation reaction with an amine compound or a halogen compound containing a terminal olefin (for example, allylamine or 6-chloro-1-hexene) in the presence of a platinum catalyst to synthesize silane compound (Step 3). Alternatively, when compound 1 is an alkoxysilane (for example, trimethoxysilane, triethoxysilane, etc.), substituents (R) may be introduced into the compound 1 by a nucleophilic substitution reaction according to the same reaction as described above, and then the resulting compound may be subjected to the hydrosilylation reaction to synthesize the silane compound 6.

Details of synthetic route 2 (Compound 1→Compound 5→Compound 7→Compound 6):

For example, when compound 1 is trichlorosilane, the compound 1 is subjected to a hydrosilylation reaction with a compound 4 (wherein Y represents a halogen atom, and m is an integer of 1 to 18) in the presence of a platinum catalyst, and accordingly a strand providing a spacer is attached thereto to obtain compound 5. Then, the substituents (R) are introduced thereto by a nucleophilic substitution reaction according to the above similar reaction to obtain compound 7. Then, the compound 7 is reacted with R¹CH (for example, methanol, ethanol, propanol, etc.) in the presence of a base, or is reacted with an alcoholate such as R¹ONa or water (R¹: hydrogen) to obtain the silane compound 6 (Lg: R¹O group).

The introduction of R¹O group (methoxy group, ethoxy group, propoxy group, etc.) can be carried out by a method of adding methanol, ethanol, propanol, or the like as the reagent to a solution containing the compound 2 (Lg: halogen atom) or the compound 4 (Lg: halogen atom); or a method of adding the compound 2 or the compound 6 dropwise to the corresponding alcohol or a solution containing the corresponding alcohol.

Details of synthetic route 3 (Synthetic route for Compound 6→silane coupling agent):

In the above-mentioned synthetic route 1 and synthetic route 2, the silane compound 6 which contains a functional group Y (an amino group or a halogen atom) may be obtained.

When the functional group Y is an amino group, various silane coupling agents can be prepared by a method of carbamoylation, amidation or ureidation of the amino group of the silane compound 6.

When the functional group Y is a halogen atom, the silane compound 6 is reacted with an ammonia or a primary amine compound, and accordingly the halogen atom is eliminated, and an amino group or an imino group (—NH—) is introduced thereto or an ether bond is introduced thereto, to obtain various silane coupling agent.

It is preferable to use a reaction solvent in any of the above-mentioned reactions. The reaction solvent is preferably an organic solvent such as pentane, hexane, heptane, toluene, tetrahydrofuran, or the like, or a mixture of two or more thereof.

The silane compound is usually purified by distillation under normal pressure or reduced pressure conditions. The obtained silane coupling agent is purified by, for example, liquid separation, distillation, or column chromatography.

(Method for Preparing Nucleic Acid)

In the method for preparing nucleic acid of the present embodiment, the nucleic acid can be synthesized with the above-mentioned inorganic porous carrier according to a publicly known method. Particularly, the preparation of nucleic acid is preferably carried out according to the phosphoramidite method. The nucleic acid synthesis method according to the phosphoramidite method is described below.

[Preparation of Solid-Phase Carrier]

A solid-phase carrier refers to a carrier wherein a nucleoside, or nucleotide in which a reactive group is protected or deprotected is bound to the amino group (—NH$_2$) contained in the above-mentioned inorganic porous carrier through a divalent group.

In this embodiment, an inorganic porous carrier that comprises a linker represented by general formula (2) wherein a mode diameter in a pore distribution as measured by mercury intrusion method is 0.04 µm to 1 µm, and also a cumulative pore volume ratio of cumulative pore volume (VB) whose pore size being within a range of 0.004 µm to 0.04 µm relative to cumulative pore volume (VA) whose pore size being within a range of 0.04 µm to 1 µm is 30% or less can be used as a solid-phase carrier.

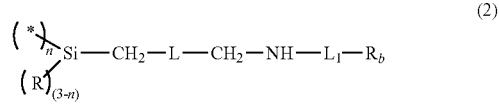

[wherein
a bond marked with * represents a linkage to the oxygen atom of a silanol group in an inorganic porous substance;
n is an integer of 1, 2 or 3;
R represents independently of each other an alkyl group containing 3 to 10 carbon atoms which may optionally have a substituent selected from an alkoxy group and a fluorine atom; a phenyl group which may optionally have a substituent selected from an alkyl group, an alkoxy group, and a fluorine atom; a hydroxyl group; or an alkoxy group containing 1 to 4 carbon atom;
L represents a single bond; an alkylene group containing 1 to 20 carbon atoms; or an alkylene group containing 2 to 20 carbon atoms which contains —CH$_2$-Q-CH$_2$— group wherein any group Q selected from the group consisting of —O—, —NH—, —NH—CO—, and —NH—CO—NH— is inserted into at least one —CH$_2$—CH$_2$— group constituting the alkylene group; providing that a carbon atom of the methylene group bound to the group Q doses not bind to another group Q at the same time;
R$_b$ represents a nucleotide or a nucleotide in which a reactive group is protected or deprotected; and
L$_1$ represents a divalent group bound to an oxygen atom of a primary or a secondary hydroxy group as R$_b$.].

In the formula (2), R and L are described in the same manner as the description of R and L in the formula (1).

In the formula (2), the divalent group L$_1$ bound to the imino group (—NH—) preferably contains a succinyl group as a functional group.

Examples of the divalent group L$_1$ typically include a succinyl linker, a universal linker, and a linking group which is composed of a universal linker and a group linking an imino group (—NH—) in the formula (2) to the universal linker.

The universal linker contains a functional group (typically, a hydroxyl group) which can form a phosphite with the hydroxyl group of the nucleotide that provides a starting point of nucleic acid synthesis, and a functional group which can bond to an amino group at the end of linker represented by the formula (1), and further contains an adjacent protected functional group (for example, a protected amino group, a protected hydroxyl group, or a protected thiol group) in the same molecule, which can nucleophilically attack a phosphorus atom of phosphoric acid under the conditions for cleaving the synthesized nucleic acid.

More specifically, examples of the divalent group L$_1$ include a linking group represented by the following formula L$_{10}$, and a linking group represented by the following formula L$_{11}$.

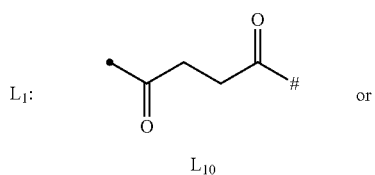

-continued

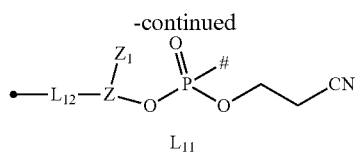

Here, in each of the formulae $L_{10}$ and $L_{11}$, the bond marked with ● represents a bond to the imino group (—NH—) in the formula (2). The bond marked with # represents a bond to an oxygen atom of a primary or secondary hydroxyl group of $R_b$ in the above formula (2).

In the formula $L_{11}$, $Z_1$ represents a protected amino group, a protected hydroxyl group, or a protected thiol group. The oxygen atom and $Z_1$ which are bound to Z represent groups which are adjacent to each other (for example, they exist in vicinal position, and carbon atoms of Z that are attached thereto are directly bound to each other).

$L_{12}$ represents a group which links the imino group (—NH—) to the universal linker (for example, represented by ●—CO(CH$_2$)$_2$CO—&; and the bond marked with & represents a bond to Z).

When the universal linker is used, even though the 3'end of the nucleic acid to be synthesized becomes any kinds of nucleoside or nucleotide, the nucleoside phosphoramidite providing the 3' end can be reacted and introduced in the same manner as the method of elongating the nucleic acid according to the usual nucleic acid automatic synthesis. Examples of such a universal linker include the compounds described in the following references, but are not limited thereto:

REFERENCE

A. P. Guzaev, and M. Manoharan, J AmChem Soc, 2003, 125, 2380-2381.

REFERENCE

R. K. Kumar, A. P. Guzaev, C. Rentel, and V. T. Ravikumar, Tetrahedron, 2006, 62, 4528.

In the formula (2), it is preferable for $R_b$ that the hydroxyl group at the 5' position of the nucleoside, which provides the starting point of the nucleic acid elongation reaction, is protected with a trityl-based protecting group (for example, 4,4'-dimethoxytrityl (DMTr) group, etc.).

Similarly, when the universal linker is used, it is preferable that the hydroxyl group, which provides the starting point of the nucleic acid elongation reaction, is protected with a trityl-based protecting group (for example, 4,4'-dimethoxytrityl (DMTr) group, etc.).

The solid-phase carrier containing the linker represented by the formula (2) is typically prepared by a condensation reaction of the inorganic porous carrier containing the linker represented by the general formula (1) with the compound ($R_b$-$L_{10}$-W). This $L_{10}$ represents a linking group represented by the above-mentioned formula $L_{10}$. W represents a reactive functional group (for example, a hydroxyl group).

When the nucleoside linker is used, the nucleoside linker corresponding to the base at the 3' end is selected depending on the sequence of RNA to be synthesized. Examples of the nucleoside linker include a nucleoside linker containing a succinyl group as a functional group to be reacted with an amino group (—NH$_2$).

Examples of the nucleoside linker containing a succinyl group are shown below.

In the following formulae, each of marks * represents a bond to the imino group (—NH—) in the above-mentioned formula (2). TBDMS refers to a tert-butyldimethylsilyl group. Ac refers to an acetyl group.

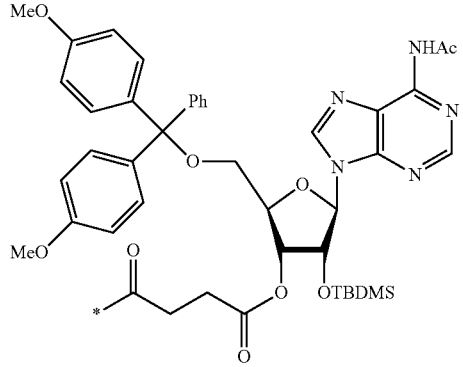

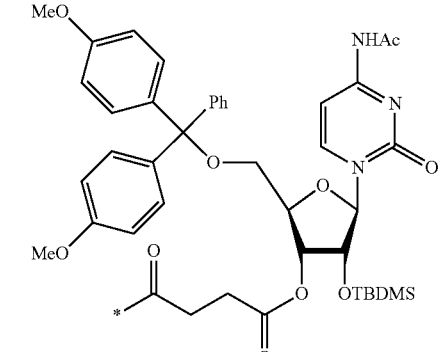

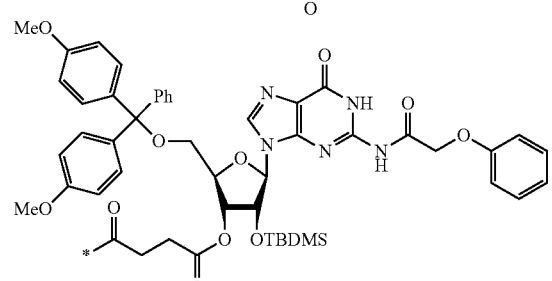

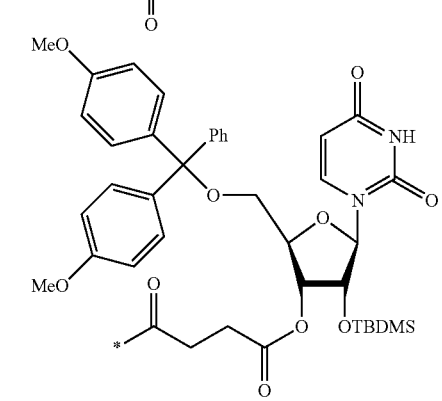

The condensation reaction as described above is carried out by mixing the inorganic porous carrier, the compound ($R_b$-$L_{10}$-W), the condensing agent and an appropriate solvent, and usually shaking the mixture at room temperature or heating the mixture to facilitate the condensation reaction. The condensation reaction may ales be carried out by allowing the mixture to stand without shaking and with stirring.

As the condensing agent for the condensation reaction, any condensing agent to be usually used for an amide condensation can be used. Specific examples of the condensing agent include N,N'-dicyclohexylcarbodiimide (DCC), N,N'-diisopropylcarbodiimide (DIC), 1-ethyl-3-(3-dimethylaminopropyl)carbodiimide hydrochloride (EDAC), 1-ethyl-3-(3-dimethylaminopropyl)carbodiimide (EDC), 1-[bis(dimethylamino)methylene]-1H-1,2,3-triazolo[4,5-b]pyridinium 3-oxide hexafluorophosphate (HATU), 1-[bis(dimethylamino)methylene]-1H-1,2,3-benzotriazolium 3-oxide hexafluorophosphate (HBTU), 1-[bis(dimethylamino)methylene)]-1H-1,2,3-triazolo[4,5-b]pyridinium 3-oxide tetrafluoroborate (TATU), 1-[bis(dimethylamino)methylene]-1H-1,2,3-benzotriazolium 3-oxide tetrafluoroborate (TBTU), (1-cyano-2-ethoxy-2-oxoethylideneaminooxy)dimethylaminomorpholinocarbenium hexafluorophosphate (COMU), O-[(ethoxycarbonyl)cyanomethyleneamino]-N,N,N',N'-tetramethyluronium hexafluorophosphate (TOTU) and the like, or a mixture of two or more thereof. Additives such as N,N-dimethyl-4-aminopyridine (DMAP) and N,N-diisopropylethylamine may be added.

The solid-phase carrier after the completion of the condensation reaction is filtered by filtration with a solvent, and collected. Examples of the solvent for filtration include acetonitrile and the like. Capping treatment to the unreacted amino group may be carried out. Examples of the capping treatment agent to be used include acetic anhydride (for example, acetic anhydride-tetrahydrofuran solution) and phenoxyacetic anhydride (for example, phenoxyacetic anhydride/N-methyl imidazole solution). The success or failure of capping can be confirmed by a ninhydrin test. When a nucleoside linker or universal linker having a protecting group such as 4,4'-dimethoxytrityl (DMTr) group is used, the quantification of the reacted nucleoside can be carried out by cleaving the DMTr group with an acid and then measuring an absorbance thereof.

The amount of $(R_b-L_1)$ supported is usually within a range of 0.1 to 5.0 μmol/m$^2$, and preferably 0.5 to 2.0 μmol/m$^2$, relative to the specific surface area per mass of the inorganic porous substance, which is determined by $N_2$ adsorption/desorption measurement.

The solid-phase carrier of the present embodiment is preferable as a substrate for a solid-phase synthesis of nucleic acid (DNA and RNA). Further, the solid-phase carrier of the present embodiment is particularly suitable for the synthesis of RNA, which has been considered to have a problem in stability as compared with DNA.

Hereinafter, the solid-phase synthesis of RNA is illustrated as an example of the preparation method, and the method for preparing nucleic acid is described with reference to a reaction route shown below (condensation reaction, oxidation, and deprotection).

Here, relative to the reaction route illustrated below, an example in which a nucleoside is used as $R_b$ in the formula (2) is shown.

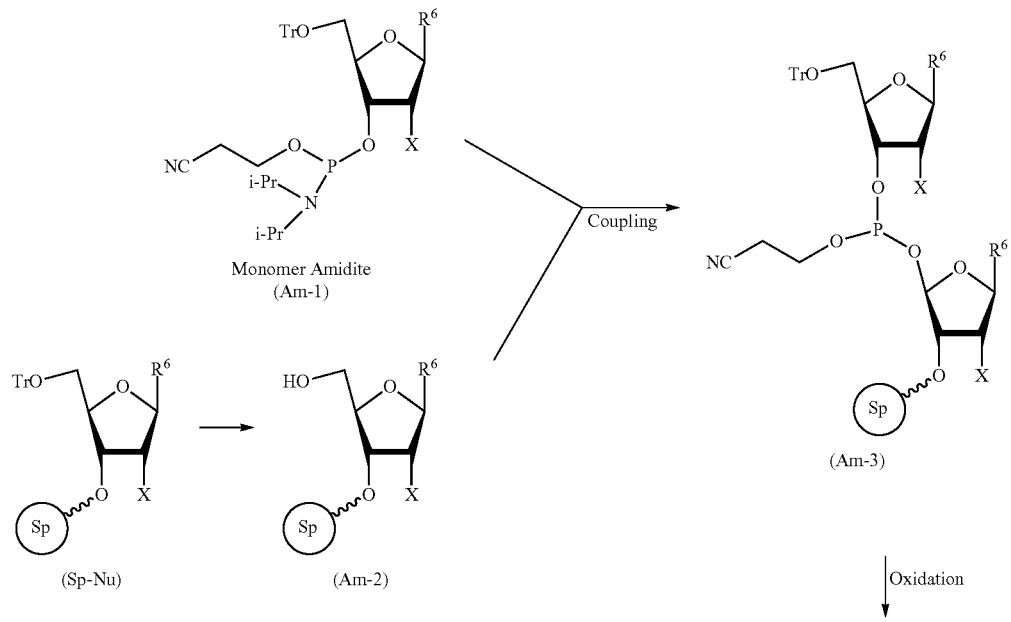

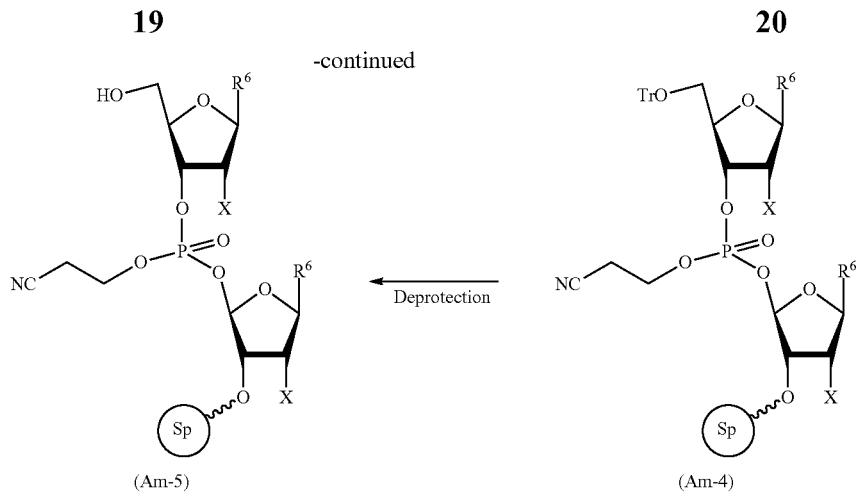

(Am-5)      ← Deprotection      (Am-4)

In the chemical formula shown in the above reaction route, $R^6$ represents a base; Tr represents a protecting group; and X represents —H, —OH or —$OR^7$ (wherein, $R^7$ represents a protecting group).

The base ($R^6$) constituting the nucleoside of the solid-phase carrier (Sp-Nu) containing the linker represented by the general formula (2) and the nucleoside of the amidite monomer (Am-1) is usually a nucleic acid, and typically a naturally-occurring base which is composed of RNA, however, may be a non-naturally-occurring base in some cases. Examples of such the non-naturally-occurring base include modified analogs of the naturally-occurring base or non-naturally-occurring base.

Examples of the base represented by $R^6$ include purine bases such as adenine, isoguanine, xanthine, hypoxanthine and guanine; and pyrimidine bases such as cytosine, uracil and thymine; and the like.

Examples of the base represented by $R^6$ further include amino derivatives such as 2-aminoadenine, 2-aminopurine, and 2,6-diaminopurine; alkyl derivatives such as 5-methyluracil, 5-methylcytosine, 7-methylguanine, 6-methylpurine, 2-propylpurine; 5-halouracil and 5-halocytosine; 5-propynyluracil and 5-propynylcytosine; 6-azauracil, 6-azacytosine and 6-azathymine; 5-uracil (pseudouracil), 4-aminoallyluracil; 8-substituted purines, for example, 8-halogenated, aminated, thiolated, thioalkylated or hydroxylated purine, or other 8-substituted purine; 5-substituted pyrimidines, for example, 5-trifluoromethylated pyrimidine, or other 5-substituted pyrimidine; 6-azapyrimidine; N-2, N-6 or 0-6 substituted purines (including 2-aminopropyladenine); dihydrouracil; 3-deaza-5-azacytosine; 7-deazaadenine; N6-methyladenine, N6,N6-dimethyladenine; 5-aminoallyl-uracil; N3-methyluracil; substituted 1,2,4-triazole; 2-pyridinone; 5-nitroindole; 3-nitropyrrole; 5-methoxyuracil; uracil-5-oxyacetic acid; 5-methoxycarbonylmethyluracil; 2-thiouracil, 5-methyl-2-thiouracil; 5-methoxycarbonylmethyl-2-thiouracil; 5-methylaminomethyl-2-thiouracil, 3-(3-amino-3-carboxypropyl)uracil; 3-methylcytosine; N4-acetylcytosine; 2-thiocytosine; N6-methyladenine; N6-isopentyladenine; 2-methylthio-N6-isopentenyladenine; N-methylguanine; O-alkylated bases, or the like; and a mixture of two or more thereof.

Further, examples of purine compounds and pyrimidine compounds include those disclosed in each of U.S. Pat. No. 3,687,808; "Concise Encyclopedia Of Polymer Science And Engineering, pp. 858-859, edited by Kroschwitz J. I., John Wiley & Sons, 1990; and Englisch et al., Angewandte Chemie, International Edition, 1991, vol. 30, p. 613.

Examples of the amidite monomer (Am-1) preferably include TBDMS amidite (TBDMS RNA Amidites, product name, ChemGenes Corporation), ACE amidite, TOM amidite, CEE amidite, CEM amidite, TEM amidite (Reviews by Chakhmakhcheva: Protective Groups in the Chemical Synthesis of Oligoribonucleotides, Russian Journal of Bioorganic Chemistry, 2013, Vol. 39, No. 1, pp. 1-21.), and EMM amidite (as described in WO2013/027843 A1), or the like, in which the protecting group $R^7$ in the compound represented by the following chemical formula (Am-1') is tert-butyldimethylsilyl (TBDMS) group, bis(2-acetoxy)methyl (ACE) group, (triisopropylsilyloxy)methyl (TOM) group, (2-cyanoethoxy)ethyl (CEE) group, (2-cyanoethoxy)methyl (CEM) group, para-tolylsulfonylethoxymethyl (TEM) group, (2-cyanoethoxy)methoxymethyl (EMM) group, or the like.

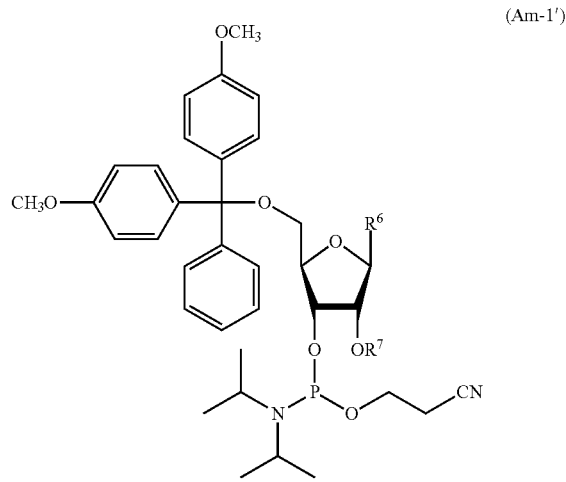

(Am-1')

[wherein, $R^7$ represents a protecting group of the hydroxyl group; and $R^6$ represents a protected nucleobase.]

The solid-phase carrier of the present embodiment may also be used to incorporate a divalent group other than a nucleoside and nucleotide into a nucleic acid sequence. For example, an amidite having a proline framework (for example, Amidite P as described later) can be incorporated into a nucleic acid sequence according to the amidite method (see the same method as the method of Example A4 of WO2012/017919 A1). Further, the amidite represented by each of the following structural formulae (Am-11), (Am-12) and (Am-13) (see Examples A1 to A3 of WO2013/103146 A1) may also be used.

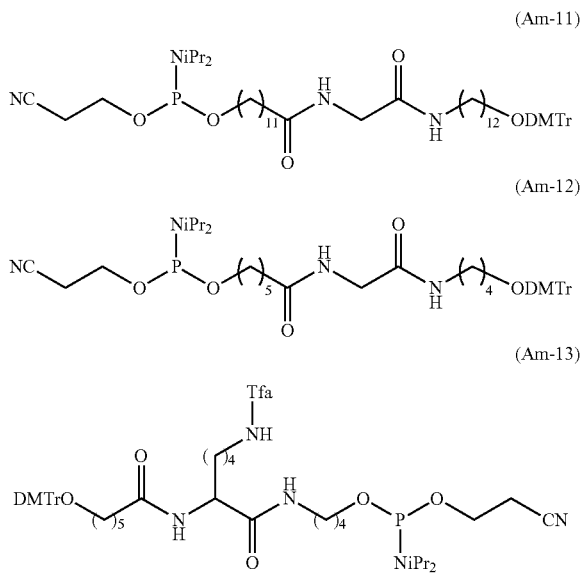

[wherein, iPr represents an isopropyl group, DMTr represents a 4,4'-dimethoxytrityl group, and Tfa represents a trifluoroacetyl group.]

[Solid-Phase Synthesis of RNA]

The solid-phase carrier (Sp-Nu) containing the linker represented by the general formula (2) is deprotected (-Tr) to obtain the solid-phase carrier (Am-2). Then, the amidite monomer (Am-1) and the solid-phase carrier (Am-2) are subjected to a condensation reaction to obtain a reaction product (Am-3). Then, the reaction product (Am-3) is oxidized to obtain the product (Am-4). Then, the product (Am-4) is deprotected (-Tr) to obtain the product (Am-5). Then, the amidite monomer (Am-1) and the product (Am-5) are further subjected to a condensation reaction to elongate the phosphodiester bond.

As described above, the hydroxyl group of the 5' position at the end of the elongated oligonucleotide strand is repeatedly subjected to a series of cycle including deprotection, condensation reaction and oxidation as many times as necessary so as to provide a desired sequence, and then the resulting product can be cleaved from the solid-phase carrier to produce a nucleic acid molecule having a desired sequence.

More specifically, a nucleic acid is prepared according to a preparation method comprising the following steps:
  step (A): a step of deprotecting the protecting group of the hydroxyl group at the 5' position of the nucleoside using the inorganic porous carrier wherein $R_b$ in the general formula (2) represents a nucleoside or nucleotide in which a hydroxyl group as a reactive group is protected;
  step (B): a condensation step of subjecting the hydroxyl group at the 5' position of the nucleoside produced in the step (A) to a condensation reaction with an amidite compound having a second nucleoside base to produce a phosphite;
  step (C): an oxidation step of oxidizing the phosphite produced in the step (B) to produce a nucleotide; and
  step (D): a step of deprotecting the protecting group of the hydroxyl group at the 5' position of the nucleotide produced in the step (C).

The preparation method comprising the above-mentioned steps (A) to (D) may optionally comprise the following steps:
  step (B'): a step of further subjecting the product produced in the step (D) to a condensation reaction with an amidite compound having a nucleoside base to be introduced in next time to produce a phosphite;
  step (C'): a step of oxidizing the phosphite produced in the step (B') to produce an oligonucleotide;
  step (D'): a step of deprotecting the protecting group of the hydroxyl group at the 5' position in the end of the oligonucleotide strand produced in the step (C'); and
  step (E): a step of carrying out a series of steps consisting of the above step (B'), step (C') and step (D') repeatedly m times (wherein m is an integer of 1 or more) to react the number of m of amidite compounds (nucleic acid elongation reaction), and then cleaving an elongated nucleic acid.

The nucleic acid elongation reaction of the present embodiment can be carried out according to the procedure of a general phosphoramidite method.

The "nucleic acid elongation reaction" herein refers to a reaction in which a nucleic acid strand, particularly RNA strand, is elongated by sequentially binding nucleotides through a phosphodiester bond. The nucleic acid elongation reaction may be carried out by means of an automatic nucleic acid synthesizer or the like that employs the phosphoramidite method.

In the deprotection step, the protecting group of the hydroxyl group at the 5' position in the end of the RNA strand supported on the solid-phase carrier is deprotected. As a general protecting group, a trityl-based protecting group (typically, a DMTr group) is used. The deprotection can be carried out with an acid. Examples of the acid for deprotection include trifluoroacetic acid, trichloroacetic acid, dichloroacetic acid, trifluoromethanesulfonic acid, methanesulfonic acid, hydrochloric acid, acetic acid, p-toluenesulfonic acid.

In the condensation step, the nucleoside phosphoramidite is bound to the hydroxyl group at the 5' position in the end of the RNA strand which is deprotected by the above-mentioned deprotection step so as to produce the phosphite. As the nucleoside phosphoramidite, a nucleoside phosphoramidite in which the hydroxyl group at the 5' position is protected with a protecting group (for example, DMTr group) is used.

Further, the condensation step can be carried out with an activator which activates the nucleoside phosphoramidite. Examples of the activator include 5-benzylthio-1H-tetrazole (BTT), 1H-tetrazole, 4,5-dicyanoimidazole (DCI), 5-ethylthio-1H-tetrazole (ETT), N-methylbenzimidazolium triflate (N-MeBIT), benzimidazolium triflate (BIT), N-phenylimidazolium triflate (N-PhIMT), imidazolium triflate (IMT), 5-nitrobenzimidazolium triflate (NBT), 1-hydroxybenzotriazole (HOBT), 5-(bis-3,5-trifluoromethylphenyl)-1H-tetrazole (Activator-42), and the like, or a mixture of two or more thereof.

After the condensation step, an unreacted hydroxyl group at the 5' position may be capped as needed. The capping can be carried out with a publicly known capping solution such as acetic anhydride-tetrahydrofuran solution, phenoxyacetic acid/N-methylimidazole solution, and the like, or a mixture of two or more thereof.

The oxidation step refers to a step of oxidizing the phosphite formed by the condensation step. The oxidation step can be carried out with an oxidizing agent. Examples of the oxidizing agent include iodine, m-chloroperbenzoic acid, tert-butylhydroperoxide, 2-butanoneperoxide, bis(trimethylsilyl)peroxide, 1,1-dihydroperoxycyclododecane, hydrogen peroxide, and the like, or a mixture of two or more thereof.

The oxidation step may be carried out after the capping operation as described above, or conversely, the capping operation may be carried out after the oxidation step, and accordingly an order of them is not limited thereto.

After the oxidation step, the method returns to the deprotection step, and the above-mentioned steps including condensation reaction, oxidation and deprotection can be repeated depending on a nucleotide sequence of RNA to be synthesized so as to synthesize RNA having a desired sequence.

After the synthesis of the RNA strand having the desired sequence is completed, the RNA strand is cleaved from the solid-phase carrier by ammonia, amines, or the like, and collected.

Examples of the amines as describe above include methylamine, ethylamine, isopropylamine, ethylenediamine, diethylamine, triethylamine, and the like, or a mixture of two or more thereof.

When the universal linker is used, after the completion of the synthesis of RNA strand, the RNA strand is cleaved from the solid-phase carrier by ammonia, amines, or the like, and the universal linker is eliminated with a nucleophile. Once the elimination is completed, the 3' position of a terminal nucleotide is changed to a hydroxyl group, and the phosphate is bound to the universal linker to form a cyclic phosphodiester. The collected RNA may be purified by a publicly known method, as needed.

With respect to the inorganic porous carrier according this embodiment as described above, it is adopted a solid-phase carrier wherein in a particular pore distribution, that is, a most frequent value (mode diameter) of a pore is included in the range of 0.04 μm to 1 μm, and also a cumulative pore volume ratio of cumulative pore volume (VB) whose pore size being within a range of 0.004 μm to 0.04 μm relative to cumulative pore volume (VA) whose pore size being within a range of 0.04 μm to 1 μm is 30% or less. The solid-phase carrier exists with a high homogeneity of pore having appropriate diameter with respect to the elongation of the target strand length, and contains very small amount of a pore having inappropriate (small with respect to a target strand length) diameter. In the pore having inappropriate pore diameter (small diameter), an elongation reaction is likely to stop on the way to the target. Accordingly, the solid-phase carrier according to this embodiment can easily elongate to a target strand length, and as a result, a purity is further improved in a preparation of RNA. Particularly, a reduction of impurities at the beginning of oligonucleic acid synthesis can be drastically achieved. Also the method for preparing RNA according to this embodiment can improve a purity in a preparation of RNA, and particularly, a long-stranded RNA can be obtained stably in high purity.

In addition, when the inorganic porous carrier of the present embodiment is applied to the nucleic acid synthesis, highly pure RNA can be obtained, even if long-stranded RNA of 40-mer or more is synthesized. The upper limit of the strand length of the RNA strand is not particularly limited, and may be, for example, 200 mer or less or 150 mer or less.

The "purity of RNA" herein refers to a percentage (%) at which the nucleic acid having the target strand length is obtained. It is determined based on an area percentage (that is, a percentage of measured area) or a 10% width of a main peak in a chromatogram obtained by liquid chromatography.

EXAMPLES

Hereinafter, the present invention is described in more detail with reference to Examples, however, the present invention should not be limited to these examples.
<Preparation of Inorganic Porous Substance>

Each of SP (1) to SP (10) as described below was used as the inorganic porous substance. In each of the inorganic porous substances SP (1) to SP (10), the most frequent value of the pore size (mode diameter; μm), the particle size (median diameter; μm), the cumulative pore volume ratio (%), the pore volume per volume (mL/mL), the specific surface area per volume ($m^2$/mL), and the porosity (%) were determined. The results are shown in Table 1.

The pore size (mode diameter; μm), the pore volume per volume (mL/mL), and the porosity (%) were determined respectively by a mercury intrusion method. The particle size (μm) was determined based on the median diameter measured by laser diffraction (scattering type). The specific surface area per volume ($m^2$/mL) was determined by multiplying the bulk density (g/mL), which was measured by the mercury intrusion method, by the specific surface area per mass the inorganic porous substance ($m^2$/g), which was measured by $N_2$ adsorption/desorption isotherm measurement.

Inorganic Porous Substance SP (1):

A molded zeolite substance was obtained in the same manner as in Example 1 described in JP 5875843 B2. The resulting molded zeolite substance was suspended in a solvent of acetonitrile to prepare a suspension. Then, the suspension was sieved with a JIS sieve having an opening size of 125 μm and successively with a JIS sieve having an opening size of 38 μm. Then, the powdery solid remaining on the sieve having an opening size of 38 μm was dried by air at room temperature to prepare the inorganic porous substance SP (1) as a white powdery solid.

Inorganic Porous Substance SP (2):

In a stainless steel autoclave with a capacity of 1.5 L, tetraethyl orthosilicate [$Si(OC_2H_5)_4$] 115 g, 40% by mass tetra-n-propyl ammonium hydroxide aqueous solution 67 g, potassium hydroxide (purity 85%) 0.7 g and water 317 g were placed, and the mixture was vigorously stirred at room temperature for 120 minutes. The molar ratios of water, tetra-n-propyl ammonium ion, hydroxide ion and potassium ion to silicon in the obtained mixed solution were 36, 0.24, 0.27 and 0.048, respectively. The mixed solution was stirred at 105° C. for 48 hours at a rotation speed of 300 rpm, and subjected to a hydrothermal reaction. The resulting reaction mixture was filtered, and washed repeatedly with pure water until the pH of the filtrate was made 9.0 or less. The obtained wet cake was dried at 110° C., and then pulverized in a mortar. The obtained pulverized substance was sieved with a sieve having an opening size of 2.36 mm and successively a sieve having an opening size of 1.00 mm. The obtained substance was calcined in a tubular furnace at 530° C. for 1 hour under nitrogen flow, and then further calcined at 530°

C. for 1 hour under flow of a mixed gas of nitrogen and air [nitrogen: air (volume ratio)=9:1] to obtain a white calcined substance.

Next, 10 g of the calcined substance as obtained above was put in a petri dish, and stood in a two-liter separable flask containing 100 mL of water, and the separable flask was closed with a lid. Then, the separable flask was placed in a constant temperature water bath at 80° C. for 5 hours. The separable flask was taken out, and allowed to cool to 20° C. The resulting solid 8 g was placed in an autoclave, and a mixed solution 222 g of 7.5% by mass ammonium nitrate aqueous solution 88 g and 25% by mass ammonia aqueous solution 134 g was added thereto, and the mixture was stirred at 90° C. for 1 hour, and then the solid was separated by filtration. The solid was further treated with the mixed solution of the ammonium nitrate aqueous solution and the ammonia aqueous solution prepared in the same manner as described above repeatedly twice, and then washed with water, and dried. Finally, the obtained white solid was pulverized in a mortar, and sieved with sieves having an opening size of 106 μm and successively an opening size of 38 μm to obtain the inorganic porous substance SP (2).

Inorganic Porous Substance SP (3):

In a stainless steel autoclave with a capacity of 1.5 L, tetraethyl orthosilicate [$Si(OC_2H_5)_4$] 155 g, 40% by mass tetra-n-propyl ammonium hydroxide aqueous solution 136 g, potassium hydroxide (purity 85%) 0.3 g and water 162 g were placed, and the mixture was vigorously stirred at room temperature for 120 minutes. The molar ratios of water, tetra-n-propyl ammonium ion, hydroxide ion and potassium ion to silicon in the obtained mixed solution were 18, 0.36, 0.38 and 0.048, respectively. The mixed solution was stirred at 105° C. for 48 hours at a rotation speed of 300 rpm, and subjected to a hydrothermal synthesis reaction. The resulting reaction mixture was filtered, and washed repeatedly with pure water until the pH of the filtrate was made 9.0 or less. The obtained wet cake was dried at 110° C., and then pulverized in a mortar. The obtained pulverized substance was sieved with a sieve having an opening size of 2.36 mm and successively a sieve having an opening size of 1.00 mm. The obtained substance was calcined in a tubular furnace at 530° C. for 1 hour under nitrogen flow, and then further calcined at 530° C. for 1 hour under flow of a mixed gas of nitrogen and air [nitrogen: air (volume ratio)=9:1] to obtain a white calcined substance.

Next, 10 g of the calcined substance as obtained above was put in a petri dish, and stood in a two-liter separable flask containing 100 mL of water, and the separable flask was closed with a lid. Then, the separable flask was placed in a constant temperature water bath at 80° C. for 5 hours. The separable flask was taken out, and allowed to cool to 20° C. The resulting solid 8 g was placed in an autoclave, and a mixed solution 222 g of 7.5% by mass ammonium nitrate aqueous solution 88 g and 25% by mass ammonia aqueous solution 134 g was added thereto, and the mixture was stirred at 90° C. for 1 hour, and then the solid was separated by filtration. The solid was further treated with the mixed solution of the ammonium nitrate aqueous solution and the ammonia aqueous solution prepared in the same manner as described above repeatedly twice, and then washed with water, and dried. Finally, the obtained white solid was pulverized in a mortar, and sieved with sieves having an opening size of 106 μm and successively an opening size of 38 μm to obtain the inorganic porous substance SP (3).

Inorganic Porous Substance SP (4):

In a stainless steel autoclave with a capacity of 1.5 L, tetraethyl orthosilicate [$Si(OC_2H_5)_4$] 115 g, 40% by mass tetra-n-propyl ammonium hydroxide aqueous solution 57 g, potassium hydroxide (purity 85%) 0.9 g and water 325 g were placed, and the mixture was vigorously stirred at room temperature for 120 minutes. The molar ratios of water, tetra-n-propyl ammonium ion, hydroxide ion and potassium ion to silicon in the obtained mixed solution were 36, 0.20, 0.24 and 0.048, respectively. The mixed solution was stirred at 105° C. for 48 hours at a rotation speed of 300 rpm, and subjected to a hydrothermal synthesis reaction. The resulting reaction mixture was filtered, and washed repeatedly with pure water until the pH of the filtrate was made 9.0 or less. The obtained wet cake was dried at 110° C., and then pulverized in a mortar. The obtained pulverized substance was sieved with a sieve having an opening size of 2.36 mm and successively a sieve having an opening size of 1.00 mm. The obtained substance was calcined in a tubular furnace at 530° C. for 1 hour under nitrogen flow, and then further calcined at 530° C. for 1 hour under flow of a mixed gas of nitrogen and air [nitrogen: air (volume ratio)=9:1] to obtain a white calcined substance.

Next, 10 g of the calcined substance as obtained above was put in a petri dish, and stood in a two-liter separable flask containing 100 mL of water, and the separable flask was closed with a lid. Then, the separable flask was placed in a constant temperature water bath at 80° C. for 5 hours. The separable flask was taken out, and allowed to cool to 20° C. The resulting solid 8 g was placed in an autoclave, and a mixed solution 222 g of 7.5% by mass ammonium nitrate aqueous solution 88 g and 25% by mass ammonia aqueous solution 134 g was added thereto, and the mixture was stirred at 90° C. for 1 hour, and then the solid was separated by filtration. The solid was further treated with the mixed solution of the ammonium nitrate aqueous solution and the ammonia aqueous solution prepared in the same manner as described above repeatedly twice, and then washed with water, and dried. Finally, the obtained white solid was pulverized in a mortar, and sieved with sieves having an opening size of 106 μm and successively an opening size of 38 μm to obtain the inorganic porous substance SP (4).

Inorganic Porous Substance SP (5):

A commercial spherical silica dispersion solution (Product name: Seehoster KE-W30, manufactured by Nippon Shokubai Co. Ltd.) 30 mL was dried at 80° C. to obtain a solid in a massive form. The obtained solids were calcined at 800° C. for 3 hours, and pulverized in a mortar, to obtain a powdered solid. The obtained powdered solids were suspended in acetonitrile solvent, and after that, the resulting suspension solutions were sieved with sieves having an opening size of 38 μm. The powdered solids remained on the sieve were air dried at room temperature to obtain the inorganic porous substance SP (5) 4 g as a white powdered solid.

Inorganic Porous Substance SP (6):

A calcined zeolite substance was obtained in the same manner as in Example 1 described in JP 5875843B2. Then, 10 g of the resulting calcined substance was put in a petri dish, and stood in a two-liter separable flask containing 100 mL of water, and the separable flask was closed with a lid. Then, the separable flask was placed in a constant temperature water bath at 80° C., and left to stand for 24 hours. The separable flask was taken out, and allowed to cool to 20° C. The resulting solid 8 g was placed in an autoclave, and a mixed solution 222 g of 7.5% by mass ammonium nitrate aqueous solution 88 g and 25% by mass ammonia aqueous solution 134 g was added thereto, and the mixture was stirred at 90° C. for 1 hour, and then the solid was separated by filtration. The solid was further treated with the mixed solution of the ammonium nitrate aqueous solution and the ammonia aqueous solution prepared in the same manner as described above repeatedly nine times, and then washed with water, and dried to obtain the inorganic porous substance SP (6).

Inorganic Porous Substance SP (7):

In a stainless steel autoclave with a capacity of 1.5 L, tetraethyl orthosilicate [$Si(OC_2H_5)_4$] 115 g, 40% by mass tetra-n-propylammonium hydroxide aqueous solution 57 g, potassium hydroxide (purity 85%) 0.9 g and water 325 g were placed, and the mixture was vigorously stirred at room temperature for 120 minutes. The molar ratios of water, tetra-n-propylammonium ion, hydroxide ion and potassium ion to silicon in the obtained mixed solution were 36, 0.20, 0.24 and 0.048, respectively. The mixed solution was stirred at 105° C. for 48 hours at a rotation speed of 300 rpm, and subjected to a hydrothermal synthesis reaction. The resulting reaction mixture was filtered, and washed repeatedly with pure water until the pH of the filtrate was made 9.0 or less. The obtained wet cake was dried at 110° C., and then pulverized in a mortar. The obtained pulverized substance was sieved with a sieve having an opening size of 2.36 mm and successively a sieve having an opening size of 1.00 mm. The obtained substance was calcined in a tubular furnace at 530° C. for 1 hour under nitrogen flow, and then further calcined at 530° C. for 1 hour under flow of a mixed gas of nitrogen and air [nitrogen: air (volume ratio)=9:1] to obtain a white calcined substance.

Next, 10 g of the calcined substance as obtained above was put in a petri dish, and stood in a two-liter separable flask containing 100 mL of water, and the separable flask was closed with a lid. Then, the separable flask was placed in a constant temperature water bath at 80° C. for 5 hours. The separable flask was taken out, and allowed to cool to 20° C. The resulting solid 8 g was placed in an autoclave, and a mixed solution 222 g of 7.5% by mass ammonium nitrate aqueous solution 88 g and 25% by mass ammonia aqueous solution 134 g was added thereto, and the mixture was stirred at 90° C. for 1 hour, and then the solid was separated by filtration. The solid was further treated with the mixed solution of the ammonium nitrate aqueous solution and the ammonia aqueous solution prepared in the same manner as described above repeatedly twice, and then washed with water, and dried. Finally, the obtained white solid was pulverized in a mortar, and sieved with sieves having an opening size of 106 μm and successively an opening size of 38 μm to obtain the inorganic porous substance SP (7).

Inorganic Porous Substance SP (8):

A porous silica was prepared by referring to a preparation method of a double pore porous substance in Example 1 described in JP 2010-120780 A1.

Ethylene-propylene-glycol brock co-polymer (Product name: Pluronic P123, manufactured by BASF Co. Ltd.) 5.5 g was dissolved in 0.01 M aqueous acetic acid solution 40 mL, and then urea 2.5 g was dissolved thereto. To the aqueous solution was added tetraethoxysilane 25 mL, and the mixture was stirred for 1 hour to obtain a solution. The resulting solution was left to stand at 60° C. for 24 hours to obtain a gel, and the gel was washed with methanol-water. The obtained gel was dried at 60° C., and calcined at 250° C. for 10 hours to an inorganic porous substance (8) as a porous silica powder.

Inorganic Porous Substance SP (9):

In a stainless steel autoclave with a capacity of 1600 L, tetraethyl orthosilicate [$Si(OC_2H_5)_4$] 186 kg, 40% by mass tetra-n-propylammonium hydroxide aqueous solution 166 kg, potassium hydroxide (purity 85%) 0.3 kg and water 490 kg were placed, and the mixture was vigorously stirred at room temperature for 120 minutes. The molar ratios of water, tetra-n-propylammonium ion, hydroxide ion and potassium ion to silicon in the obtained mixed solution were 37, 0.36, 0.39 and 0.049, respectively. The mixed solution was stirred at 105° C. for 12 hours at a rotation speed of 60 rpm, and subjected to a hydrothermal synthesis reaction. The resulting reaction mixture was washed with pure water similarly to the above-mentioned method for preparing Inorganic porous substance SP (2). After washing, a slurry containing crystals was recovered. The slurry was spray-dried with an Atomizer-type spray dryer to mold it to a particle form. The resulting products were calcined at 550° C. for 2.5 hours under nitrogen flow, and next, were calcined at 550° C. for 2.5 hours under a mixed gas flow [nitrogen:air (by volume)=3:1] to obtain a calcined product as white substance.

Inorganic Porous Substance SP (10):

As the inorganic porous substance SP (10), a commercially available spherical silica gel powder (trade name: M.S.GEL, produced by AGC Si-Tech Co., Ltd.) was used.

[Measurement of Pore Distribution by Mercury in Method]

With respect to the inorganic porous substance SP (10) to the inorganic porous substance SP (4), a pore distribution of about 0.004 to 200 μm of pore size (value obtained by calculating differentially a pore volume by a pore size) was determined by mercury intrusion method.

The above-mentioned measurement was used with Auto-PoreIV9520 (manufactured by Micromaritics). As a pretreatment, a constant-temperature drying was carried out on the inorganic porous substance at 150° C. for 4 hours.

The pore size was calculated by the following equation (A).

$$D = -4\sigma \times \cos\theta / P \tag{A}$$

P: Pressure, D: Pore diameter, σ: Surface tension of mercury, θ: Contact angle between mercury and sample, In this measurement, the surface tension of mercury: σ was 0.48 N/m, and the contact angle between mercury and sample was 140°.

By measuring a pore distribution by the above-mentioned mercury intrusion method, the most frequent value of pore size (mode diameter, μm), a porosity (%), and a cumulative pore volume ratio of cumulative pore volume (VB) whose pore size being within a range of 0.004 μm to 0.04 μm relative to cumulative pore volume (VA) whose pore size being within a range of 0.04 μm to 1 μm, respectively were determined. The results are shown in Table 1.

Most Frequent Value (Mode Diameter):

The most frequent value of pore size was determined from a value of X-axis at a peak top in the pore size distribution obtained by the mercury intrusion method (a graph in which the X-axis is a value of the pore size and the Y-axis is a value obtained by differentiating the pore volume by the pore size).

The porosity ratio (%) was calculated by multiplying the bulk density (g/mL) with the cumulative pore volume (mL/g) which is included within a range of 0.004 μm to 200 μm.

Cumulative Pore Volume Ratio:

The cumulative pore volume ratio (%) was calculated by the following equation: VB/VA×100.

<Silane Coupling Agent>

As the silane coupling agent, the ingredient (C1) and ingredient (C2) as described below were used.

Ingredient (C1):

3-Aminopropyldiisopropylethoxysilane which was commercially available was purchased and used.

Ingredient (C2):

3-Aminopropyltriethoxysilane (TCI, CAS RN: 919-30-2, product code: A0439) was used.

<Method for Preparing Inorganic Porous Substance (Inorganic Porous Carrier) which Supports a Linker>

The inorganic porous carrier of each of examples was obtained by treating the surface of any one of the inorganic porous carriers SP (1) to SP (10) as produced above with any one of the ingredients (C1) to (C2) as the silane coupling agents.

Example 1

The inorganic porous substance SP (1) 2.00 g was placed in a four-necked flask, and toluene 100 mL was added thereto. The ingredient (C1) 4.8 mg was further added thereto under stirring, and the mixture was stirred at room temperature for 3 hours. Then, the reaction solution was filtered, and washed with toluene, and then the residue was dried under reduced pressure to obtain the inorganic porous carrier of Example 1.

Example 2

The inorganic porous carrier of Example 2 was obtained in the same manner as the preparation method of Example 1 except for that the inorganic porous substance SP (1) was replaced with the inorganic porous substance SP (2) (2.00 g).

Example 3

The inorganic porous carrier of Example 3 was obtained in the same manner as the preparation method of Example 1 except for that the inorganic porous substance SP (1) was replaced with the inorganic porous substance SP (3) (2.00 g) and the addition amount of the ingredient (C1) was changed to 6.8 mg.

Example 4

The inorganic porous carrier of Example 4 was obtained in the same manner as the preparation method of Example 1 except for that the inorganic porous substance SP (1) was replaced with the inorganic porous substance SP (4) (2.00 g) and the addition amount of the ingredient (C1) was changed to 4.5 mg.

Example 5

The inorganic porous carrier of Example 5 was obtained in the same manner as the preparation method of Example 1 except for that the inorganic porous substance SP (1) was replaced with the inorganic porous substance SP (5) (1.00 g) and the addition amount of the ingredient (C1) was changed to 2.4 mg.

Example 6

The inorganic porous carrier of Example 6 was obtained in the same manner as the preparation method of Example 1 except for that the inorganic porous substance SP (1) was replaced with the inorganic porous substance SP (6) (2.00 g) and the addition amount of the ingredient (C1) was changed to 6.8 mg.

Example 7

The inorganic porous carrier of Example 7 was obtained in the same manner as the preparation method of Example 1 except for that the inorganic porous substance SP (1) was replaced with the inorganic porous substance SP (7) (0.40 g) and the addition amount of the ingredient (C1) was changed to 1.2 mg.

Example 8

The inorganic porous carrier of Example 8 was obtained in the same manner as the preparation method of Example 1 except for that the inorganic porous substance SP (1) was replaced with the inorganic porous substance SP (9) (1.00 g) and the addition amount of the ingredient (C1) was changed to 7.0 mg.

Example 9

The inorganic porous carrier of Example 9 was obtained in the same manner as the preparation method of Example 1 except for that the inorganic porous substance SP (1) was replaced with the inorganic porous substance SP (10) (1.00 g) and the addition amount of the ingredient (C1) was changed to 2.4 mg.

Comparative Example 1

The inorganic porous carrier of Comparative Example 1 was obtained in the same manner as the preparation method of Example 1 except for that the inorganic porous substance SP (1) was replaced with the inorganic porous substance SP (8) (2.42 g) and the ingredient (C1) was replaced with the ingredient (C2) (44.7 mg).

Comparative Example 2

The inorganic porous carrier of Comparative Example 2 was obtained in the same manner as the preparation method of Example 1 except for that the inorganic porous substance SP (1) was replaced with the inorganic porous substance SP (8) (2.00 g) and the addition amount of the ingredient (C1) was changed to 1.2 mg.

Comparative Example 3

The inorganic porous carrier of Comparative Example 3 was obtained in the same manner as the preparation method of Example 1 except for that the inorganic porous substance SP (1) was replaced with the inorganic porous substance SP (8) (2.00 g) and the addition amount of the ingredient (C1) was changed to 1.2 mg (which was the same as the inorganic porous carrier of comparative example 2).

<Preparation of Solid-Phase Carrier>

U-succinate (5'-O-dimethoxytrityl-2'-O-tert-butyldimethylsilyl-3'-O-succinyluridine) 25.1 mg, 1-[bis(dimethylamino)methylene]-1H-1,2,3-benzotriazolium 3-oxide hexafluorophosphate (HBTU) 12.5 mg, N,N-diisopropylethylamine 5.9 µL and acetonitrile 2.7 mL were mixed, and the inorganic porous carrier 300.0 mg of each of Examples 1 to 10 and Comparative Examples 1 to 4 was added to the mixture.

The mixture was left to stand at 25° C. for 18 hours, and then filtered, and the solid (residue) was washed with acetonitrile 10 mL. A solution 1 mL of acetic anhydride and 2,6-lutidine in THF (volume ratio of acetic anhydride/2,6-lutidine/THF: 1/1/8) and a solution 1 mL of N-methyl imidazole in THF (volume ratio of N-methyl imidazole/THF: 16/84) were added to the washed solid. The mixture was left to stand for 1 minute, and then filtered, and the solid was washed with acetonitrile 10 mL. The washed solid was dried under vacuum to obtain the solid-phase carrier in which the nucleoside was supported on the inorganic porous carrier.

An aqueous 70% perchloric acid solution was diluted with methanol to prepare a solution of 30% perchloric acid/methanol. The solid-phase carrier 10 mg which supported the nucleoside, as prepared above, was placed in a measuring flask, and was diluted to 10 mL with the solution of 30% perchloric acid/methanol. The resulting solution was further diluted 10-fold with the solution of 30% perchloric acid/methanol, and then an absorbance thereof at 498 nm was measured, and the support density of nucleoside was calculated based on the following formula. The results are shown in Table 1.

Support Density of Nucleoside[μmol/m$^2$] =

$$\frac{(14.3 \times (\text{Absorbance at } 498 \text{ nm}) \times 10 \times 10)}{(\text{Mass of Solid-phase Carrier(mg)}) \times (\text{Specific Surface Area of Inorganic Porous Carrier(m}^2/\text{g)} \div 1000)}$$

<Solid-Phase Synthesis of Oligonucleic Acid>

```
Sequence (A):
                                  (SEQ ID NO: 1, 2)
5'-GCAGAGUACACACAGCAUAUACC-P-
GGUAUAUGCUGUGUGUACUCUGCUU-3' (49-mer).

(SEQ ID NO: 1)
GCAGAGUACACACAGCAUAUACC
and (SEQ ID NO: 2)
GGUAUAUGCUGUGUGUACUCUGCUU.

Sequence (B):
                                  (SEQ ID NO: 3)
5'-AUAACUCAAUUUGUAAAAAAGUUUUAGAGCUAGAAAUAGCAAGUUA
AAAUAAGGCUAGUCCGUUAUCAACUUGAAAAAGUGGCACCGAGUCGGUG
CUUUUUUU-3' (103-mer).
```

In the above sequence (A), P represents a binding moiety separated with wavy lines in the following structure.

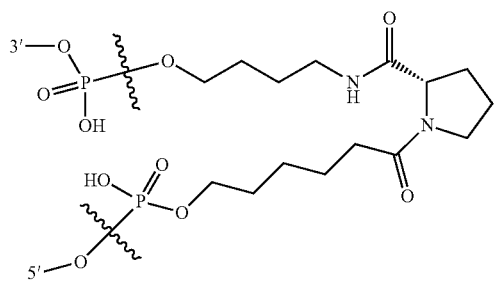

The oligonucleotide consisting of the sequence (A) or the sequence (B) was synthesized from the 3' side to the 5' side according to the phosphoramidite method by means of a nucleic acid synthesizer (trade name: NTS M-4-MX-E, produced by Nihon Techno Service Co., Ltd.) (See the reaction route (condensation reaction, oxidation, and deprotection as described above)).

Each of solid-phase carriers as prepared above was used for the above solid-phase synthesis.

As the amidite monomer, the adenosine EMM amidite (described in Example 4 of US2012/035246 A1), the cytidine EMM amidite (described in Example 3 of the same US patent literature), the guanosine EMM amidite (described in Example 5 of the same US patent literature), the uridine EMM amidite (described in Example 2 of the same US patent literature) and amidite P (described in WO2017/188042 A1) as shown below were used.

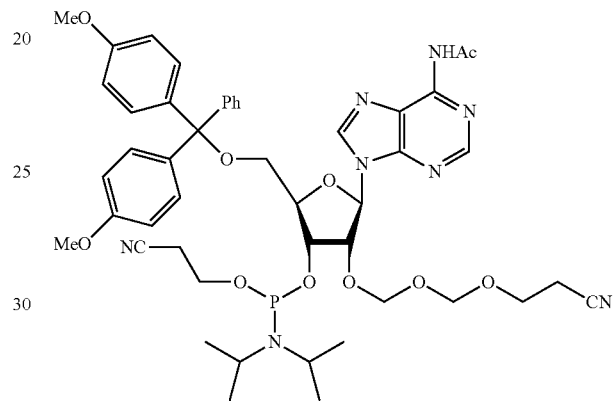

Adenosine EMM Amidite

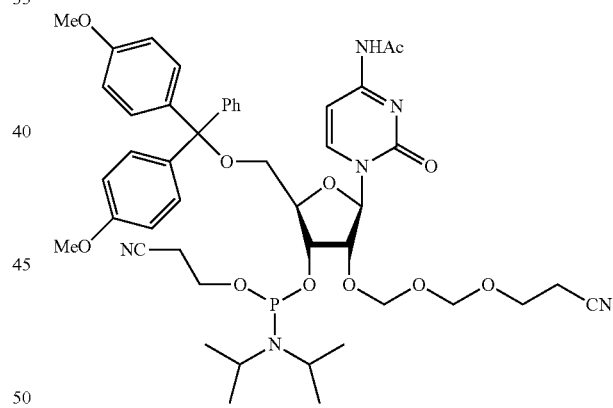

Cytidine EMM Amidite

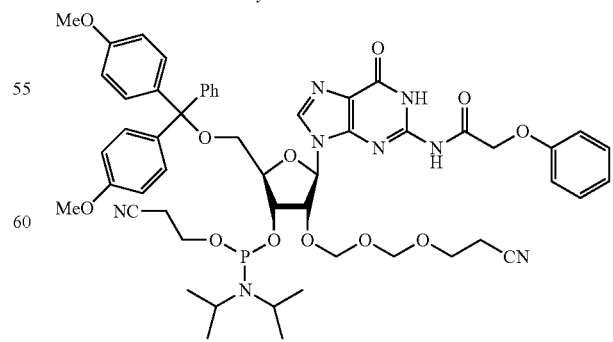

Guanosine EMM Amidite

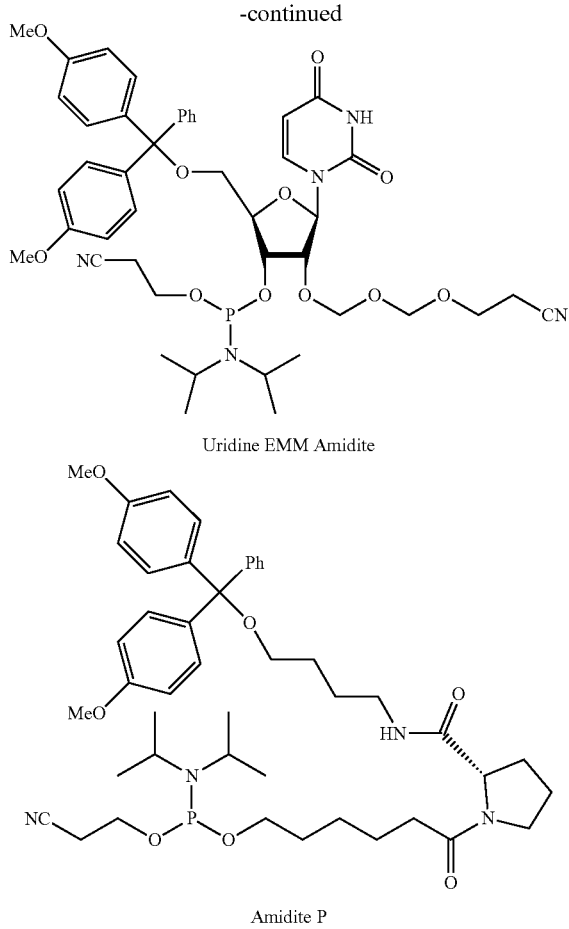

Uridine EMM Amidite

Amidite P

Further, in the solid-phase synthesis, a solution of high purity trichloroacetic acid in toluene was used as a deblocking solution, 5-benzylmercapto-1H-tetrazole was used as a condensing agent, an iodine solution was used as an oxidizing agent, and a phenoxyacetic acid solution and an N-methyl imidazole solution were used as a capping solution.

The solid-phase carrier after the completion of synthesis was placed in a glass vial with a lid, and a solution of 28% $NH_4OH$ and EtOH at a ratio of 1:1 to 2:1 was added thereto. Then, the mixture was left to stand at 40° C. for 4 hours. The solution after the completion of reaction was filtered, and washed with water and EtOH successively. The resulting solution was dried to obtain a crude oligonucleotide having a protected group. Then, the crude oligonucleotide was deprotected by the treatment with tetra-n-butyl ammonium fluoride (TBAF) in the presence of nitromethane to obtain the crude product.

[Measurement of Oligonucleic Acid Purity]

The determination of the purity of oligonucleic acid was carried out by high performance liquid chromatography HPLC (wavelength 260 nm, column DNAPac™ PA100 4×250 mm).

The above-mentioned crude products were separated into each of ingredients by the above HPLC, and then the purity of oligonucleic acid was calculated from a percentage of area value of main product having a target strand length relative to the total area value of the obtained chromatogram. The results are shown in Table 1.

TABLE 1

| | Inorganic Porous Carrier represented by General Formula (1) | | | | Pore Size mode diameter (μm) | Particle Size median diameter (μm) | Cumulative Pore Volume Ratio (%) | Pore Volume per Volume (mL/mL) | Surface Area per Volume (m²/mL) | Porosity (%) | Carrier Density of Nucleoside (μmol/m²) | Chain Length of Oligonucleic Acid | Purity of Oligonucleic Acid (%) Half Value Width of Main Peak |
|---|---|---|---|---|---|---|---|---|---|---|---|---|---|
| | Inorganic Porous Substance | Substance | n = 1 R, R | L | | | | | | | | | |
| Example 1 | SP(1) | Zeolite | Isopropyl Group | $CH_2$ | 0.081 | 48 | 7.9 | 0.29 | 8.4 | 69 | 0.65 | 49mer (RNA) | 57.8 |
| Example 2 | SP(2) | Zeolite | Isopropyl Group | $CH_2$ | 0.078 | 72 | 15.3 | 0.32 | 11.3 | 76 | 0.36 | 49mer (RNA) | 46.2 |
| Example 3 | SP(3) | Zeolite | Isopropyl Group | $CH_2$ | 0.052 | 85 | 20.2 | 0.24 | 13.8 | 81 | 0.48 | 49mer (RNA) | 54.9 |
| Example 4 | SP(4) | Zeolite | Isopropyl Group | $CH_2$ | 0.1 | 68 | 15.7 | 0.23 | 6.1 | 79 | 0.4 | 49mer (RNA) | 46.2 |
| Example 5 | SP(5) | Silica Gel | Isopropyl Group | $CH_2$ | 0.06 | 82 | 16.4 | 0.18 | 8.9 | 65 | 0.49 | 49mer (RNA) | 54.5 |
| Example 6 | SP(6) | Zeolite | Isopropyl Group | $CH_2$ | 0.11 | 48 | 9.6 | 0.34 | 7.7 | 78 | 1.03 | 103mer (RNA) | 38.1 |
| Example 7 | SP(7) | Zeolite | Isopropyl Group | $CH_2$ | 0.16 | 48 | 11.1 | 0.27 | 9.9 | 80 | 0.49 | 103mer (RNA) | 31.6 |

TABLE 1-continued

| | Inorganic Porous Carrier represented by General Formula (1) | | | | Pore Size mode diameter (μm) | Particle Size median diameter (μm) | Cumulative Pore Volume Ratio (%) | Pore Volume per Volume (mL/mL) | Surface Area per Volume (m²/mL) | Porosity (%) | Carrier Density of Nucleoside (μmol/m²) | Chain Length of Oligonucleic Acid | Purity of Oligonucleic Acid (%) Half Value Width of Main Peak |
|---|---|---|---|---|---|---|---|---|---|---|---|---|---|
| | Inorganic Porous Substance | Substance | n = 1 R, R | L | | | | | | | | | |
| Example 8 | SP(9) | Zeolite | Isopropyl Group | CH$_2$ | 0.071 | 62 | 16.0 | 0.38 | 13.8 | 85 | 0.68 | 49mer (RNA) | 42.8 |
| Example 9 | SP(10) | Silica Gel | Isopropyl Group | CH$_2$ | 0.11 | 40 | 5.9 | 0.38 | 5.8 | 81 | 0.71 | 49mer (RNA) | 50.5 |
| Comparative Example 1 | SP(8) | Silica Gel | Ethoxy Group | CH$_2$ | 0.13 | 49 | 31.9 | 0.29 | 57 | 77 | 0.33 | 49mer (RNA) | 39.2 |
| Comparative Example 2 | SP(8) | Silica Gel | Isopropyl Group | CH$_2$ | 0.13 | 49 | 31.9 | 0.26 | 57 | 77 | 0.17 | 49mer (RNA) | 39.2 |
| Comparative Example 3 | SP(8) | Silica Gel | Isopropyl Group | CH$_2$ | 0.13 | 49 | 31.9 | 0.26 | 57 | 77 | 0.17 | 103mer (RNA) | 48.2 |

According to the results shown in Table 1, it is possible to confirm that the purity of the oligonucleic acid is higher in the case of use of the solid-phase carriers of Examples 1 to 9 than in the case of use of the solid-phase carriers of Comparative Examples 1 to 3.

Accordingly, it is possible to conclude that the solid-phase carrier used in the present invention can further improve the purity in the preparation of nucleic acid.

INDUSTRIAL APPLICABILITY

The present invention provides a method for preparing nucleic acid, which can improve the purity even in the synthesis of long-stranded nucleic acid. The nucleic acid obtained by the inorganic porous carrier and the preparation method using the same is useful as a raw material for pharmaceutical products.

Sequence Listing Free Text

SEQ ID NOs: 1 to 3 in the sequence listing represent the base sequences of oligonucleotides prepared according to the preparation method of the present invention.

---

The invention claimed is:

1. An inorganic porous carrier, comprising:
a linker of formula (1); and
an inorganic porous substance connected to the linker,
wherein the inorganic porous substance has a mode diameter in a pore distribution as measured by mercury intrusion method from 0.04 μm to 1 μm, and
the inorganic porous substance has a cumulative pore volume ratio of 30% or less, where the cumulative pore volume ratio is a ratio of cumulative pore volume VB whose pore size is within a range of 0.004 μm to 0.04 μm to cumulative pore volume VA whose pore size is within a range of 0.04 μm to 1 μm,

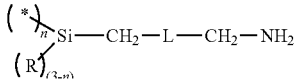

(1)

wherein,
a bond marked with * is a linkage to an oxygen atom of a silanol group in the inorganic porous substance;
n is an integer of 1, 2 or 3;
R is independently of each other an alkyl group including 3 to 10 carbon atoms which may optionally have a substituent selected from the group consisting of an alkoxy group and a fluorine atom; a phenyl group which may optionally have a substituent selected from the group consisting of an alkyl group, an alkoxy group, and a fluorine atom; a hydroxyl group; or an alkoxy group including 1 to 4 carbon atom; and
L is a single bond; an alkylene group of 1 to 20 carbon atoms; or an alkylene group including 2 to 20 carbon atoms which includes —CH$_2$-Q-CH$_2$— group wherein Q is selected from the group consisting of —O—, —NH—, —NH—CO— and —NH—CO—NH—, Q is inserted into at least one of —CH$_2$-CH$_2$— group constituting the alkylene group, and a carbon atom of a methylene group bonded to Q is not bonded to another group Q.

2. The inorganic porous carrier according to claim 1, wherein the inorganic porous substance has a specific surface area per volume of 0.1 m$^2$/mL-100 m$^2$/mL.

3. The inorganic porous carrier according to claim 1, wherein the inorganic porous substance has a pore volume per volume of 0.05 mL/mL-0.6 mL/mL.

4. The inorganic porous carrier according to claim 1, wherein the inorganic porous substance has a porosity of 50% or more.

5. The inorganic porous carrier according to claim 1, wherein the inorganic porous substance has a median diameter of 1 μm-1000 μm.

6. The inorganic porous carrier according to claim 1, wherein the inorganic porous substance comprises at least one selected from the group consisting of silica, silica gel, zeolite, and glass.

7. An inorganic porous carrier, comprising:
a linker of formula (2); and
an inorganic porous substance connected to the linker,
wherein the inorganic porous substance has a mode diameter in a pore distribution as measured by mercury intrusion method from 0.04 μm to 1 μm, and
the inorganic porous substance has a cumulative pore volume ratio of 30% or less, where the cumulative pore volume ratio is a ratio of cumulative pore volume VB whose pore size is within a range of 0.004 μm to 0.04 μm to cumulative pore volume VA whose pore size is within a range of 0.04 μm to 1 μm,

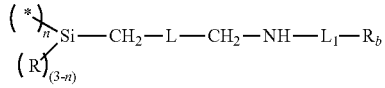

(2)

wherein,
a bond marked with * is a linkage to an oxygen atom of a silanol group in the inorganic porous substance;
n is an integer of 1, 2 or 3;
R is independently of each other an alkyl group including 3 to 10 carbon atoms which may optionally have a substituent selected from the group consisting of an alkoxy group and a fluorine atom; a phenyl group which may optionally have a substituent selected from the group consisting of an alkyl group, an alkoxy group, and a fluorine atom; a hydroxyl group; or an alkoxy group including 1 to 4 carbon atom;
L is a single bond; an alkylene group including 1 to 20 carbon atoms; or an alkylene group including 2 to 20 carbon atoms which includes —CH$_2$-Q-CH$_2$— group wherein Q is selected from the group consisting of —O—, —NH—, —NH—CO—, and —NH—

CO—NH—, Q is inserted into at least one —CH$_2$-CH$_2$— group constituting the alkylene group, and a carbon atom of a methylene group bonded to Q is not bonded to another group Q;

R$_b$ is a nucleoside or a nucleotide; and

L$_1$ is a divalent group bonded to an oxygen atom of a primary or a secondary hydroxy group of R$_b$.

8. The inorganic porous carrier according to claim 7, wherein L$_1$ includes a succinyl group as a functional group.

9. The inorganic porous carrier according to claim 7, wherein the linker has a density of 0.1 µmol/m$^2$-5.0 µmol/m$^2$ relative to a specific surface area per mass of the inorganic porous substance.

10. The inorganic porous carrier according to claim 7, wherein the inorganic porous substance has a specific surface area per volume of 0.1 m$^2$/mL-100 m$^2$/mL.

11. The inorganic porous carrier according to claim 7, wherein the inorganic porous substance has a pore volume per volume of 0.05 mL/mL-0.6 mL/mL.

12. The inorganic porous carrier according to claim 7, wherein the inorganic porous substance has a porosity of 50% or more.

13. The inorganic porous carrier according to claim 7, wherein the inorganic porous substance has a median diameter of 1 µm-1000 µm.

14. The inorganic porous carrier according to claim 7, wherein the inorganic porous substance comprises at least one selected from the group consisting of silica, silica gel, zeolite, and glass.

15. A method for preparing a nucleic acid with the inorganic porous carrier of the formula (2) of claim 2, wherein R$_b$ is a nucleoside or a nucleotide, which includes a hydroxyl group as a reactive group that is protected, the method comprising:

deprotecting a protecting group of the hydroxyl group at a 5' position of the nucleoside of R$_b$;

subjecting the hydroxyl group at the 5' position to a condensation reaction with an amidite compound having a nucleoside base to produce a phosphite;

oxidizing the phosphite to produce a nucleotide including a protected hydroxyl group at a 5' position thereof; and deprotecting a protecting group of the protected hydroxyl group at the 5' position of the nucleotide to obtain a deprotected product.

16. The method according to claim 15, further comprising:

(B') subjecting the deprotected product to a condensation reaction with an amidite compound having a nucleoside base to produce a phosphite;

(C') oxidizing the phosphite produced in (B') to produce an oligonucleotide including a protected hydroxyl group at a 5' position at an end thereof; and (D') deprotecting a protecting group of the protected hydroxyl group at the 5' position at the end of the oligonucleotide to obtain a deprotected product.

17. The method according to claim 16, further comprising:

repeating (B'), (C') and (D') to produce an elongated nucleic acid; and cleaving the elongated nucleic acid from the inorganic porous carrier.

18. The method according to claim 17, wherein the cleaving of the elongated nucleic acid is performed by ammonia or an amine.

* * * * *